(12) United States Patent
Lee et al.

(10) Patent No.: US 12,377,318 B2
(45) Date of Patent: Aug. 5, 2025

(54) ELECTRONIC APPARATUS AND OPERATION METHOD FOR PROVIDING OF WORKOUT GUIDE THEREOF

(71) Applicant: Samsung Electronics Co., Ltd., Gyeonggi-do (KR)

(72) Inventors: Hongji Lee, Gyeonggi-do (KR); Jeongmin Park, Gyeonggi-do (KR)

(73) Assignee: Samsung Electronics Co., Ltd., Suwon-si (KR)

(*) Notice: Subject to any disclaimer, the term of this patent is extended or adjusted under 35 U.S.C. 154(b) by 407 days.

(21) Appl. No.: 18/109,978

(22) Filed: Feb. 15, 2023

(65) Prior Publication Data

US 2023/0191198 A1    Jun. 22, 2023

Related U.S. Application Data

(63) Continuation of application No. PCT/KR2021/018435, filed on Dec. 7, 2021.

(30) Foreign Application Priority Data

Dec. 17, 2020  (KR) ........................ 10-2020-0177741

(51) Int. Cl.
*A63B 24/00*    (2006.01)
*A61B 5/00*    (2006.01)
(Continued)

(52) U.S. Cl.
CPC ...... *A63B 24/0062* (2013.01); *A61B 5/02108* (2013.01); *A61B 5/1118* (2013.01);
(Continued)

(58) Field of Classification Search
CPC ........ A63B 24/0062; A63B 2024/0065; A61B 5/02108; A61B 5/1118; A61B 5/742;
(Continued)

(56) References Cited

U.S. PATENT DOCUMENTS

| 6,918,879 B2 | 7/2005 | Ting et al. |
|---|---|---|
| 10,660,534 B2 | 5/2020 | Lee et al. |

(Continued)

FOREIGN PATENT DOCUMENTS

| CN | 104188639 B | 2/2017 |
|---|---|---|
| CN | 110176291 A | 8/2019 |

(Continued)

OTHER PUBLICATIONS

Extended European Research Report dated Mar. 11, 2024.

*Primary Examiner* — John R Downey
(74) *Attorney, Agent, or Firm* — Cha & Reiter, LLC.

(57) ABSTRACT

A wearable electronic device and method for the same are disclosed. The wearable device includes a memory, housing, photoplethysmogram (PPG) sensor, display and processor. The processor implements the method, including: receiving a PPG signal via the PPG sensor, detecting blood pressure values for a plurality of consecutive time periods based on characteristic information detected from the received PPG signal, in response to detecting termination of an exercise event, generating an exercise parameter determination model based on blood pressure characteristic information generated from the detected blood pressure values after the detected termination, and control the display to display information generated from the exercise parameter determination model.

20 Claims, 15 Drawing Sheets

(51) Int. Cl.
    *A61B 5/021*         (2006.01)
    *A61B 5/11*          (2006.01)

(52) U.S. Cl.
    CPC ............ *A61B 5/742* (2013.01); *A61B 5/0006* (2013.01); *A61B 5/681* (2013.01); *A63B 2024/0065* (2013.01)

(58) Field of Classification Search
    CPC ..... A61B 5/0006; A61B 5/681; A61B 5/0205; A61B 5/021; A61B 5/02416; A61B 2503/10
    See application file for complete search history.

(56) References Cited

U.S. PATENT DOCUMENTS

| | | | |
|---|---|---|---|
| 10,722,125 | B2 | 7/2020 | Tal et al. |
| 11,311,777 | B2 | 4/2022 | Yun et al. |
| 2010/0005117 | A1* | 1/2010 | Stut ........................ G16H 20/30 |
| | | | 707/E17.044 |
| 2013/0261405 | A1 | 10/2013 | Lee et al. |
| 2017/0043217 | A1 | 2/2017 | Lee |
| 2019/0159682 | A1 | 5/2019 | Nakajima et al. |
| 2019/0350464 | A1 | 11/2019 | Jeon et al. |
| 2019/0374816 | A1* | 12/2019 | Yun ...................... A61B 5/0205 |
| 2020/0383588 | A1 | 12/2020 | Fujita et al. |

FOREIGN PATENT DOCUMENTS

| | | |
|---|---|---|
| CN | 110322947 B | 7/2022 |
| JP | 2017176541 A | 10/2017 |
| JP | 2019-122502 A | 7/2019 |
| JP | 6659831 B2 | 3/2020 |
| KR | 10-0809953 B1 | 3/2008 |
| KR | 10-2013-0111713 A | 10/2013 |
| KR | 10-2016-0091694 A | 8/2016 |
| KR | 10-2016-0107752 A | 9/2016 |
| KR | 10-2017-0056397 A | 5/2017 |
| KR | 10-2019-0131306 A | 11/2019 |
| KR | 10-2019-0138969 A | 12/2019 |
| KR | 10-2197102 B1 | 12/2020 |
| KR | 10-2021-0148267 A | 12/2021 |

\* cited by examiner

FIG.10A

ELECTRONIC APPARATUS AND OPERATION METHOD FOR PROVIDING OF WORKOUT GUIDE THEREOF

CROSS-REFERENCE TO RELATED APPLICATIONS

This application is a continuation of International Application No. PCT/KR2021/018435 designating the United States, filed on Dec. 7, 2021, in the Korean Intellectual Property Receiving Office and claiming priority to Korean Patent Application No. 10-2020-0177741, filed on Dec. 17, 2020, in the Korean Intellectual Property Office, the disclosures of which are incorporated by reference herein in their entireties.

TECHNICAL FIELD

The present disclosure relates to biometric monitoring in electronic devices, and, more particularly, to biometric-based exercise guidance in electronic devices.

BACKGROUND

User interest in health has grown in recent times. Accordingly, biometric-related functions have been implemented in consumer-grade electronic devices. Such electronic devices may be coupled to a user's body to collect the user's biometric information, which may then be used to provide various health-related information. For example, the electronic device may include a biometric sensor, which may take readings from the user's body that can be used to calculate blood pressure. In addition, this information can be leveraged in other ways, such as to provide prompts and notifications to the user, based on the calculated blood pressure.

One such electronic device may include an automatic electronic blood pressure gauge or an ambulatory blood pressure monitoring (ABPM) device, for measuring the blood pressure. The automatic electronic blood pressure gauge enables a patient to measure his/her blood pressure using a blood pressure gauge at a specific time. If the user wears a cuff on his/her body, the ABPM may periodically and automatically measure the user's blood pressure.

It may be desirable to integrate blood pressure monitoring and management with electronically-assisted exercise guidance and feedback. For example, a hypertensive patient who relies upon electronic blood pressure management may wish to exercise, but there is a risk in that they may overextend themselves in exercise if reliant on blood pressure-based metrics derived merely from biometric heart-rate information. In addition, it may also be desirable to continuously monitor blood pressure after an exercise session, to detect and calibrate the relationship between exercise and the user's blood pressure. However, a typical household blood pressure gauge is not portable and requires manual user control to measure their blood pressure at the correct time. Furthermore, the ABPM may be uncomfortable to wear during exercise activity, because the cuff is designed to squeeze a portion of the user's body.

SUMMARY

Certain embodiments described in the present disclosure may provide a technique for continuously monitoring blood pressure through biometrics without disrupting the user.

A wearable device in an embodiment is disclosed, and may include: a memory, a housing, photoplethysmogram (PPG) sensor exposed to an external environment of the wearable device through at least part of the housing, a display, and at least one processor operatively connected with the display, the memory and the PPG sensor, wherein the at least one processor is configured to: receive a PPG signal via the PPG sensor, detect blood pressure values for a plurality of consecutive time periods based on characteristic information detected from the received PPG signal, in response to detecting termination of an exercise event, generate an exercise parameter determination model based on blood pressure characteristic information generated from the detected blood pressure values after the detected termination, and control the display to display information generated from the exercise parameter determination model.

An method of a wearable device according to an embodiment is disclosed, and may include: receiving a photoplethysmogram (PPG) signal via a PPG sensor, receiving blood pressure values for a plurality of consecutive time periods based on characteristic information detected from the received PPG signal, in response to detecting termination of an exercise event, generating an exercise parameter determination model based on blood pressure characteristic information generated from the received blood pressure values after the detected termination, and displaying information generated from the exercise parameter determination model on a display.

An electronic device in an embodiment is disclosed, and may include: a memory, a communication circuit configured to communicate with a wearable device, a display, and at least one processor operatively connected with the display, the communication circuit and the display, wherein the at least one processor is configured to receive a photoplethysmogram (PPG) signal value from the wearable device, via the communication circuit, detect blood pressure values for a plurality of consecutive time periods based on the PPG signal value, in response to detecting termination of an exercise event, generate an exercise parameter determination model based on blood pressure characteristic information generated from the detected blood pressure values after the detected termination, and display information generated from the exercise parameter determination model.

An electronic device in certain embodiments according to the present disclosure may provide continuous blood pressure monitoring, allowing improved exercise promptings and guidance, and thus improve the user's physiological health.

Furthermore, various effects obtained directly or indirectly from the present disclosure may be provided.

BRIEF DESCRIPTION OF DRAWINGS

FIG. 10A is a diagram for showing a user interface (UI) displayed on a display, in an electronic device according to a first embodiment.

In regard to the description of the drawings, the same or similar reference numerals may be used for the same or similar components.

DETAILED DESCRIPTION

Figure 1:
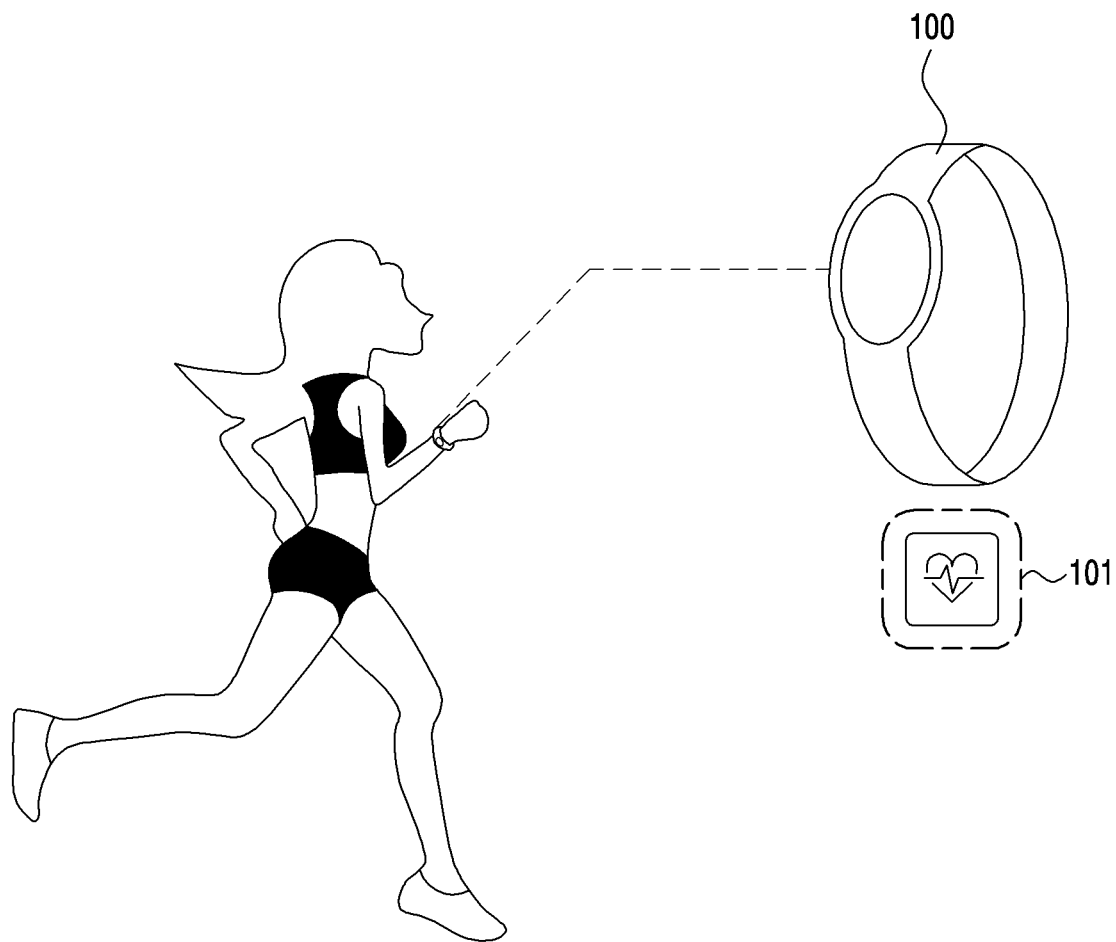
FIG. 1 is a diagram showing a workout by mounting a wearable device on a body part according to an embodiment.

FIG. 1 is a diagram illustrating a user exercising while mounting a wearable device on a body part, according to an embodiment.

According to an embodiment, a wearable device 100 of FIG. 1 may include a smart watch as shown. It is understood the disclosure is not limited thereto, and the wearable device 100 may take other various forms which attach to a user's body.

According to an embodiment, the wearable device 100 may be attached to a portion of the user's body, according to a shape and/or a size of the wearable device 100. For example, the wearable device 100 may be attached to a user's head, arm, waist, leg, back of a hand, or a finger.

According to an embodiment, the wearable device 100 may obtain user's biometric data using one or more sensors included in the wearable device 100. For example, the wearable device 100 may obtain biometric data 101 such as user's heart rate, electrodermal activity (EDA), electrocardiography (ECG), and blood flow rate, and oxygen saturation $SpO_2$.

Figure 2:
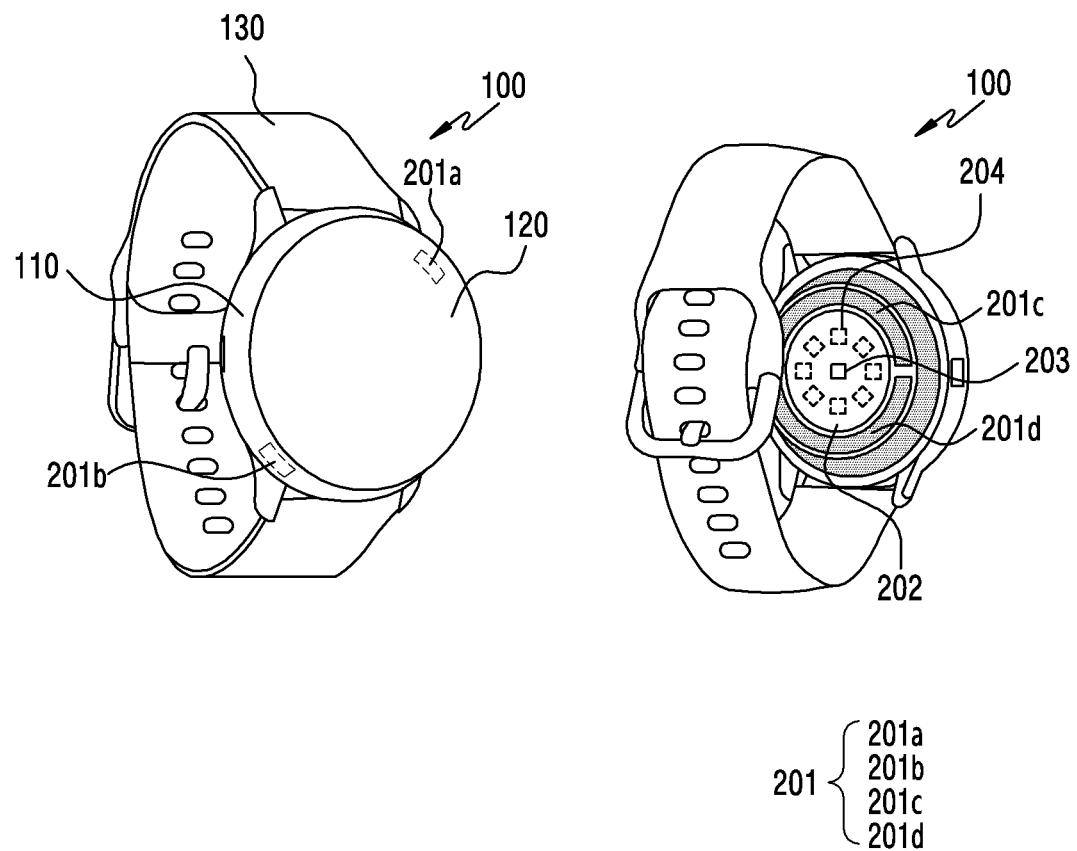
FIG. 2 is a perspective view of a wearable device according to an embodiment.

FIG. 2 is a perspective view of a wearable device according to an embodiment.

Referring to FIG. 2, the wearable device 100 may include a housing 110, a display 120, a strap 130, electrodes 201, and a photoplethysmogram (PPG) sensor 202. According to an embodiment, the wearable device 100 may omit at least one of the illustrated components, or further include other components not illustrated in FIG. 2.

According to an embodiment, the housing 110 may include an upper surface, a lower surface, and a side surface surrounding a space defined between the upper surface and the lower surface. According to an embodiment, the display 120 may be exposed as to be visible to an external environment of the device through one area of the housing 110.

According to an embodiment, the electrodes 201 may be disposed in at least part of the housing 110. In an embodiment, a first electrode 201a and a second electrode 201b may be disposed in the upper surface or the side surface of the housing 110, and a third electrode 201c and a fourth electrode 201d may be disposed in the lower surface of the housing 110. According to an embodiment, the electrodes 201 may be electrically connected with an ECG sensor (not shown). According to an embodiment, a shape or a size of the electrode may be configured variously.

According to an embodiment, the PPG sensor 202 may be exposed through the lower surface of the housing 110. According to an embodiment, the PPG sensor 202 may include a light emitting module 203 and a light receiving module 204. According to an embodiment, the light emitting module 203 may include a light emitting diode (LED) and a laser diode (LD) having various wavelengths. For example, the light emitting module 203 may include an infrared ray (IR) LED, a red LED, a green LED, and/or a blue LED. According to an embodiment, the light receiving module 204 may include at least one photodiode (PD).

According to an embodiment, the display 120 may display various information, including the user's monitored biometric data obtained through the biometric sensor.

According to an embodiment, the wearable device 100 may provide an exercise guide to the user through the display 120, as generated by a workout parameter determination module operating in consideration of the user's biometric data.

According to an embodiment, according to a user input to a part of the housing 110 (e.g., a bezel thereof), or by an input to the display (e.g., a touch input) the wearable device 100 may switch a screen output through the display 120. For example, the wearable device 100 may switch a clock screen to a biometric data screen (e.g., showing blood pressure value) in response to reception of the user's input.

According to an embodiment, the strap 130 may be coupled to at least part of the housing 110, and detachably fasten the wearable device 100 to a user's body part (e.g., a wrist, an ankle). According to an embodiment, the user of the wearable device 100 may adjust the tightness of the strap 130 to achieve a secure and comfortable fit.

The aforementioned structure of the wearable device 100 is a mere example, and the wearable device 100 may be implemented differently from FIG. 2, in certain embodiments. The wearable device 100 may have various adequate shapes and/or structures to carry out a method for biometric data measurement disclosed in this document.

Figure 3:
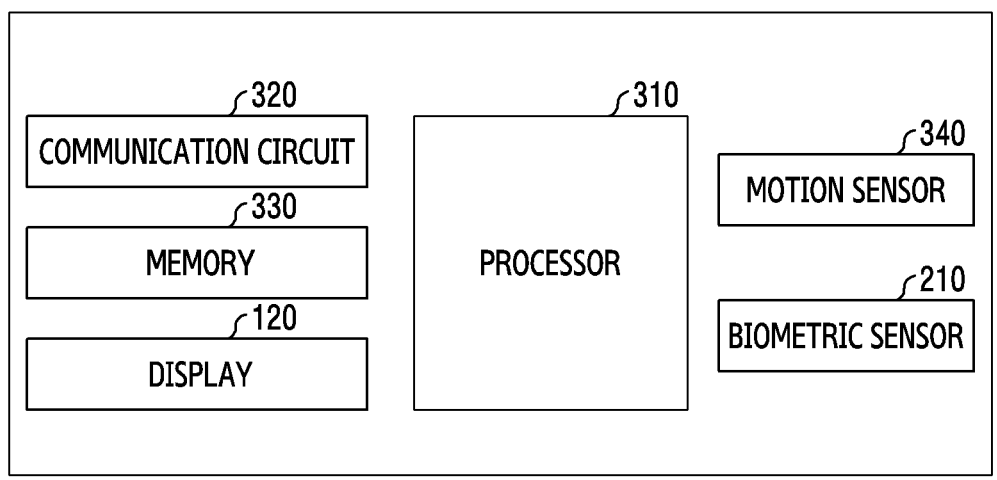
FIG. 3 is a block diagram of a wearable device according to an embodiment.

FIG. 3 is a block diagram of a wearable device according to an embodiment.

Referring to FIG. 3, the wearable device 100 according to an embodiment may include a processor 310, a communication circuit 320, a memory 330, a display 120, a motion sensor 340, or a biometric sensor 210. In certain embodiments, the wearable device 100 may include an additional component besides the components shown in FIG. 3, or may omit at least one of the components shown in FIG. 3.

According to an embodiment, the processor 310 may execute operations or data processing related to control and/or communication of at least one other components of the wearable device 100 using instructions stored in the memory 330. According to an embodiment, the processor 310 may include at least one of a central processing unit (CPU), a graphics processing unit (GPU), a micro controller unit (MCU), a sensor hub, a supplementary processor, a communication processor, an application processor, an application specific integrated circuit (ASIC), and field programmable gate arrays (FPGA), and may have a plurality of cores.

According to an embodiment, the processor 310 may obtain detailed information on the user's exercise based on exercise-related movements detected via the motion senor 340. According to an embodiment, the processor 301 may obtain a biometric signal (e.g., a PPG signal) from the biometric sensor 210 (e.g., the PPG sensor 202). Specific details related to the operations of the processor 310 shall be described later by referring to FIG. 6.

According to an embodiment, the display 120 may display various contents (e.g., a text, an image, a video, an icon, and/or a symbol, etc.). According to an embodiment, the display 120 may include a liquid crystal display (LCD), an LED display, a quantum dot (QD), a micro LED (μ LED), or an organic LED (OLED) display. According to an embodiment, the display 120 may display the user's biometric information according to a command of the processor 310. For example, the display 120 may provide a user's blood pressure value per time period. According to an embodiment, the display 120 may provide a guide for the workout program according to a command of the processor 310.

According to an embodiment, the display 120 may include touch circuitry configured to detect a touch, or sensor circuitry (e.g., a pressure sensor) configured to measure a force level generated by the touch.

According to an embodiment, the communication circuit 320 may wirelessly communicate with an external electronic device. According to an embodiment, the communication circuit 320 may transmit data to the electronic device (e.g., a smart phone), and receive data from the electronic device. According to an embodiment, the communication circuit 320 may communicate directly with the electronic device, and communicate via other external device. For example, the communication circuit 320 may be one of a cellular module, a WiFi module, a Bluetooth module, a global navigation satellite system (GNSS)/radio navigation satellite service (RNSS) module or a near field communication (NFC) module.

According to an embodiment, the memory 330 may store various data acquired or used by at least one component (e.g., the processor) of the wearable device 100. For example, the memory 330 may store the data acquired by the motion sensor 340 and/or the biometric sensor 210.

According to an embodiment, the motion sensor 340 may obtain information pertaining to the user's activity via detected movement-related information thereof. According to an embodiment, the motion sensor 340 may include at least one of an acceleration sensor, a gyroscope sensor, a barometer, or a magnetic sensor. According to an embodiment, the motion sensor 340 may obtain information related to a plurality of activities (e.g., exercises, traveling, etc.) performed by the user of the wearable device 100 based on acceleration information, location information and/or time information. For example, the wearable device 100 may recognize the activity such as sleeping, movement by car, exercise, working and/or resting. According to an embodiment, the wearable device 100 may further detect time and location information related to each executed activity.

According to an embodiment, the biometric sensor 210 may include at least one biometric sensor for measuring the blood pressure. For example, the biometric sensor 210 may include the PPG sensor 202, an ECG sensor, a pressure sensor or a microphone, and may measure the blood pressure using a combination of one or two or more of them. According to an embodiment, the PPG sensor 202 may include the light emitting module 203 and the light receiving module 204. According to an embodiment, a signal processing module (not shown) may control the light emitting module 203 and the light receiving module 204. According to an embodiment, the signal processing module may include a sensor driver controller for directly controlling the sensor and an analog to digital converter (ADC). According to an embodiment, the signal processing module may further include other configurations (e.g., an amplifier and/or a filter, etc.) not shown in FIG. 3. According to an embodiment, the signal processing module may be implemented with a microprocessor.

According to an embodiment, the signal processing module may operate at least one LED of the light emitting module 203. According to an embodiment, the signal processing module may process (e.g., amplify and/or filter) a signal detected by the light receiving module 204. For example, the signal processing module may convert a current signal detected by the light receiving module 204 to a voltage signal, and convert the processed voltage signal to a digital signal.

Figure 4:
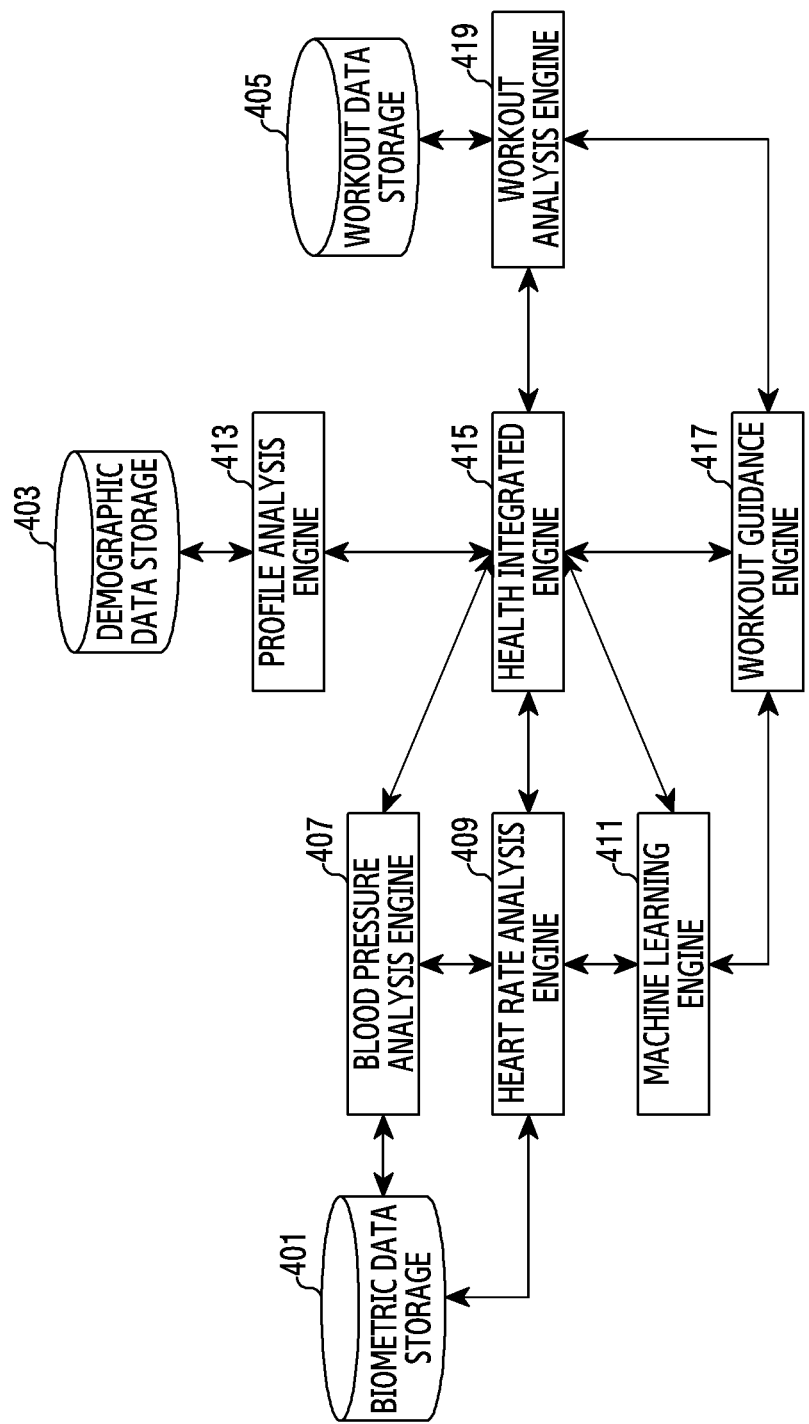
FIG. 4 is a block diagram for illustrating a configuration of a wearable device divided per module based on operations of the wearable device according to an embodiment.

FIG. 4 is a block diagram for illustrating a configuration of a wearable device divided per module based on operations of the wearable device according to an embodiment.

Referring to FIG. 4, the wearable device 100 according to an embodiment may include a biometric data storage 401, a demographic data storage 403, a workout data storage 405, a blood pressure analysis engine 407, a heart rate analysis engine 409, a machine learning engine 411, a profile analysis engine 413, a health integrated engine 415, a workout guidance engine 417, or a workout analysis engine 419. In certain embodiments, the wearable device 100 may include an additional component beyond the components illustrated in FIG. 4, and/or may omit at least one of the components shown in FIG. 4. The configuration shown in FIG. 4 may not be necessarily implemented with hardware physically divided. To implement the components shown in FIG. 4, the processor (e.g., the processor 310 of FIG. 3) of the wearable device 100 may execute commands (e.g., instructions) stored in a memory (e.g., the memory 330 of FIG. 3), and control hardware (e.g., the communication circuit 320 of FIG. 3) related to the function. For example, the biometric data storage 401, the demographic data storage 403 and the workout data storage 405 may be stored in one storage medium.

Figure 11:
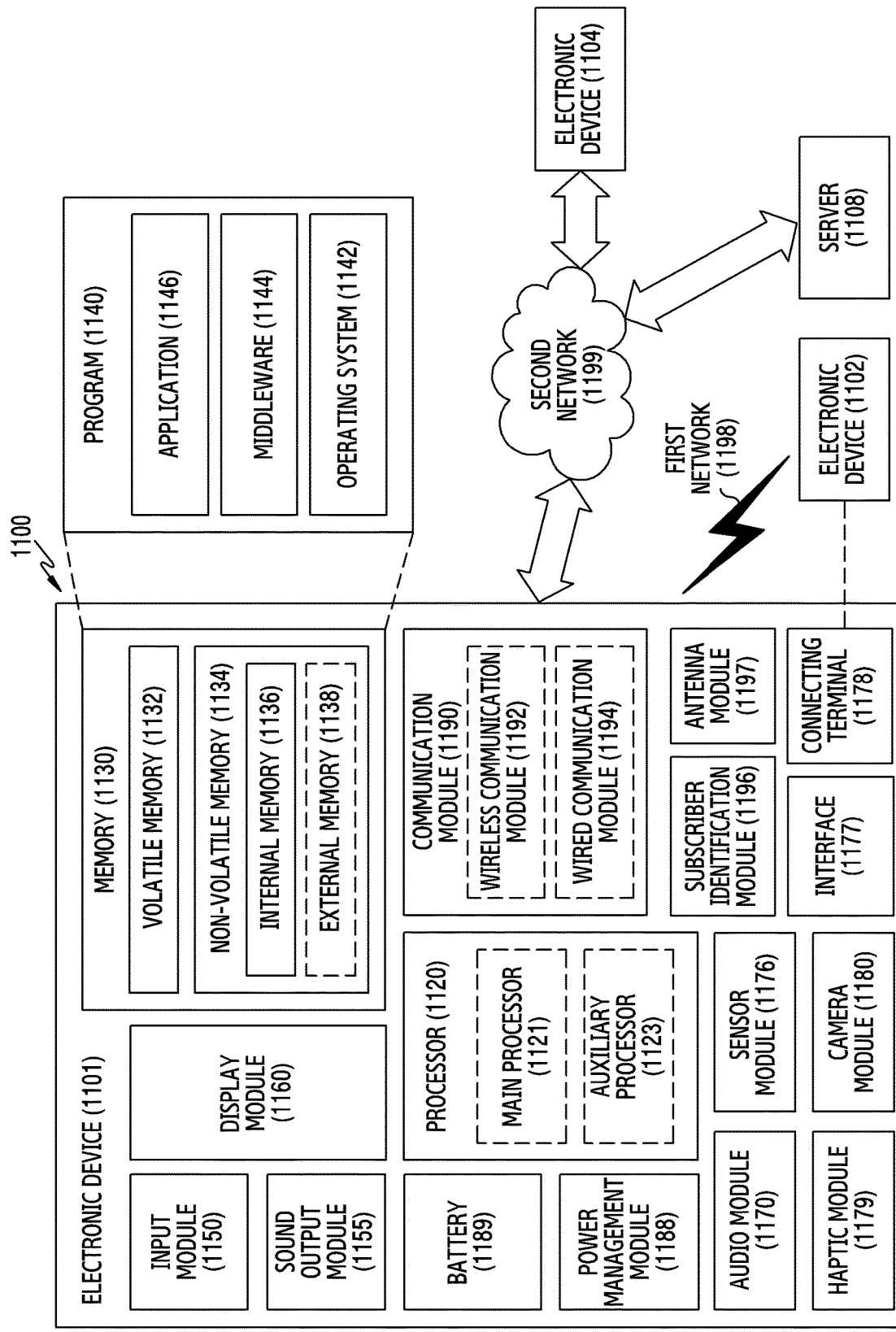
FIG. 11 is a block diagram of an electronic device in another network environment according to an embodiment.

According to some embodiment, at least part of the components shown in FIG. 4 may be implemented by at least one external electronic device (e.g., the electronic device 1102, 1104 or the server 1108 of FIG. 11).

According to an embodiment, the biometric data storage 401 may store a biometric waveform measured using the PPG sensor 202. Also, the biometric data storage 401 according to an embodiment may store a blood pressure and/or a heart rate calculated from the measured biometric waveform.

According to an embodiment, the demographic data storage 403 may store user's profile information and blood pressure medicine information. For example, the demographic data storage 403 may store the profile information such as a height, a weight, an age, or a gender, as inputted by the user, and the blood pressure medicine information.

According to an embodiment, the workout data storage 405 may store various workout information (e.g., exercise information). For example, the workout data storage 405 may store a workout type, a workout difficulty, a workout part, or unit information corresponding to the workout. Also, for example, the workout data storage 405 may store parameters related to the workout, as collected through the motion sensor 340 during performance of the exercises and/or the workout.

According to an embodiment, the blood pressure analysis engine 407 may analyze the received biometric information and generate estimates from the analysis. According to an embodiment, the blood pressure analysis engine 407 may estimate the user's blood pressure by analyzing the biometric information as continuously monitored through the user's daily life (e.g., assuming the wearable electronic device 100 is continuously worn). For example, the blood pressure analysis engine 407 may estimate the blood pressure by analyzing the received biometric information in response to entering a measuring mode, and estimate the blood pressure by analyzing the received biometric information in response to detecting a "wearing state" in which the wearable device 100 is worn by the user. According to an embodiment, the blood pressure analysis engine 407 may estimate the blood pressure by analyzing the biometric waveform stored in the biometric data storage 401.

According to an embodiment, the heart rate analysis engine 409 may estimate the user's heart rate from the biometric waveform (e.g., the PPG signal) stored in the biometric data storage 401, and determine a maximum heart rate of the workout based on the accumulated data. According to an embodiment, the heart rate analysis engine 409 may measure the heart rate in real-time from the biometric waveform stored in the biometric data storage 401.

According to an embodiment, the machine learning engine 411 may execute machine learning on information provided to the health integrated engine 415. For example, the machine learning engine 411 may process the workout information and the measured blood pressure by estimating causal relationships between exercise activity and user blood pressure as indicated by patterns within the information, and generate a predictive model that can define a performance parameter for a next workout or exercise, which may be effective to better control the user's blood pressure within safe margins during execution of the next workout or exercise. According to an embodiment, the prediction model for determining the workout parameter may include a workout parameter determination model. According to an embodiment, the machine learning engine 411 may organize a workout program by analyzing the profile information, the maximum heart rate in the workout, the workout related parameter (e.g., a workout event, a workout intensity, etc.) or the continuous blood pressure value.

According to an embodiment, the machine learning engine 411 may be implemented in the external electronic device (e.g., the electronic device 1102, 1104 or the server 1108 of FIG. 11), and the learning and/or the operation of the machine learning engine 411 may be performed in the external electronic device. The wearable device 100 may transmit the obtained information to the external electronic device, to facilitate determination of the desired performance parameters for the next exercise or workout, which will improve control of the user's blood pressure. The external electronic device may execute machine learning on the received data utilizing the workout parameter determination model.

According to an embodiment, the profile analysis engine 413 may analyze one or more workout parameters affecting the workout in the profile information. For example, the profile analysis engine 413 may analyze the workout parameter based on the profile information such as the user's height, weight, age, gender, or blood pressure medication time received from the demographic data storage 403. For example, the profile analysis engine 413 may exclude blood pressure information measured in a designated time period after the blood pressure medication in the measured blood pressure information from the analysis target for analyzing the blood pressure control effect of the workout. According to an embodiment, the profile analysis engine 413 may provide the analyzed workout parameter information to the health integrated engine 415. According to an embodiment, since a half-life differs depending on the type of the medicine, the time for which the blood pressure drop and the effect of the workout last may differ depending on the medication time. For example, the blood pressure medication time may correspond to a time for which the medication affects a user's physiological state (e.g., a cardiovascular state), a user's medication time (e.g., a previous medication time, a designated next medication time), or a difference of the user's medication time (e.g., a previous medication time, a designated next medication time) and a current time.

For example, information of the blood pressure medication time may be prestored in a memory (e.g., the memory 330 of FIG. 3). The profile analysis engine 413 (or the processor (e.g., the processor 310 of FIG. 3)) may store the blood pressure medication time information in the memory, and determine a relationship between blood pressure characteristic information and workout information (e.g., a workout event, a workout intensity) based on the stored blood pressure medication time information.

According to an embodiment, the health integrated engine 415 may map a relationship between the biometric information (e.g., the blood pressure value, the heart rate data, the profile information) and the workout information (e.g., the workout event, the workout intensity) based on the machine learning. According to an embodiment, the health integrated engine 415 may receive the blood pressure data of a plurality of consecutive periods (e.g., a normal period, a pre-workout period, a workout period, a post-workout period, a sleeping period) from the blood pressure analysis engine 407. According to an embodiment, the health integrated engine 415 may receive maximum heart rate data of the workout from the heart rate analysis engine 409. According to an embodiment, the health integrated engine 415 may receive profile data (e.g., a height, a weight, an age, a gender, a blood pressure medication time) from the profile analysis engine 413. According to an embodiment, the health integrated engine 415 may receive the conducted workout data (e.g., a workout event, a workout unit) from the workout analysis engine 419. The health integrated engine 415 may determine a workout parameter of the workout to recommend to the user for the blood pressure control using the prediction model generated by the machine learning engine 411.

According to an embodiment, the workout guidance engine 417 may organize the workout program for personalized blood pressure management. According to an embodiment, the workout guidance engine 417 may determine the workout parameter based on the information received from the machine learning engine 411, the health integrated engine 415 and the workout analysis engine 419. According to an embodiment, the workout guidance engine 417 may output a workout program selected based on the determined workout parameter through an application. For example, the workout guidance engine 417 may output guidance related to execution of a workout or exercise by the user, as per a current workout event, such as providing a count of repetitions, an exercise time (e.g., a lap time or total time), or a sequence of exercises to perform.

According to an embodiment, the workout analysis engine 419 may determine the workout being conducted by the user through the motion sensor 340 and analyze parameters of the workout determined to have been conducted. According to an embodiment, the workout analysis engine 419 may determine the conducted workout based on the measured value from the motion sensor 340 and the workout information stored in the workout data storage 405.

Figure 5A:
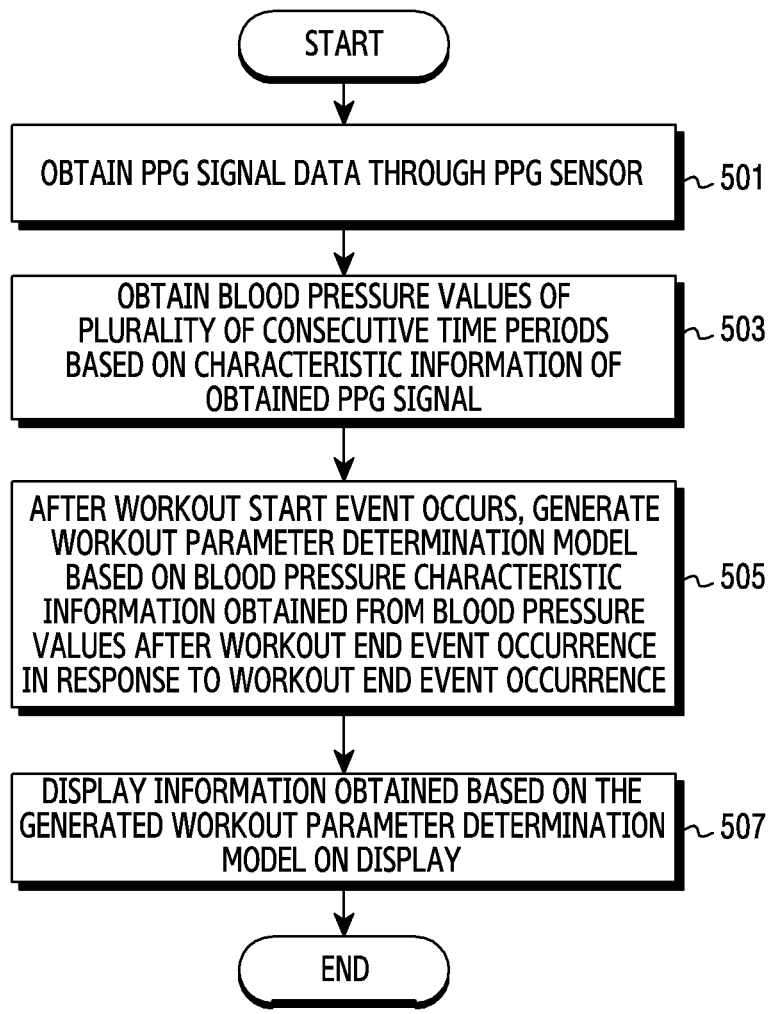
FIG. 5A is a flowchart of generating a workout parameter determination model based on obtained biometric data, in a wearable device according to an embodiment.

FIG. 5A is a flowchart of generating a workout parameter determination model based on obtained biometric data, in a wearable device according to an embodiment.

Referring to FIG. 5A, a processor (e.g., the processor 310 of FIG. 3) according to an embodiment may obtain PPG signal data through the PPG sensor 202, in operation 501. According to an embodiment, the wearable device 100 may obtain the PPG signal data through a PPG sensor (e.g., the sensor 202 of FIG. 2) which is secured to the user's body (e.g., a wrist, via the strap 130). According to an embodiment, the processor 310 may continuously obtain the PPG signal data.

According to an embodiment, the processor 310 may automatically initiate the measurement of the user's biometric waveform from the PPG sensor 202 in response to detecting that the wearable device 100 is worn (e.g., a "wearing state"). According to an embodiment, the processor 310 may automatically terminate the measurement of the biometric waveform in response to detecting that the wearable device 100 is no longer worn. According to another embodiment, the processor 310 may obtain the user's biometric waveform from the PPG sensor 202 in response to executing the measurement mode in the wearable device 100. For example, a scheme for entering the measurement mode may be one of executing a biometric measurement menu, executing an application, or a user input (e.g., a drag input) to the display 120. According to an embodiment, the processor 310 may terminate the biometric waveform measurement in response to detecting end of the measurement mode.

The processor 310 according to an embodiment may obtain (or detect) blood pressure values for a plurality of consecutive time periods based on characteristic information of the obtained PPG signal, in operation 503. According to an embodiment, the processor 310 may calculate the blood pressure value based on the characteristic information of the obtained PPG signal. According to an embodiment, the processor 310 may detect a maximum peak amplitude and a peak time index, a maximum peak amplitude and a peak time index of a systolic period and a maximum peak amplitude and a peak time index of a diastolic period, and calculate the blood pressure value by calculating a difference or a ratio between the detected amplitude values and a difference between the detected time values. For example, if the blood pressure is high, the maximum peak amplitude value may increase, and the difference of the peak time index and the peak time index of the systolic period may decrease.

According to an embodiment, the processor 310 may continue to receive the PPG signal, monitor the same, and divide the received PPG signal into a plurality of consecutive time periods and store them in memory. For example, the plurality of the consecutive time periods may include a normal period, a pre-workout period, a workout period, a post-workout period and a sleeping period. According to an embodiment, the processor 310 may divide and store the user's blood pressure medication time into a plurality of time periods together with the blood pressure value. According to an embodiment, the processor 310 may calculate at least one of a minimum blood pressure, a maximum blood pressure and an average blood pressure for each period.

In operation 505, after detecting a workout start event (e.g., an event indicating initiation of exercise), the processor 310 according to an embodiment may generate a workout parameter determination model based at least on the blood pressure characteristic information obtained from the blood pressure values. The model may further be generated detecting termination of exercise via a "workout end" event.

According to an embodiment, the processor 310 may detect the workout start event through the motion sensor 340. According to an embodiment, the processor 310 may automatically determine the workout event and/or posture based on a user's movement as detected through the motion sensor 340. For example, automatic recognition workout events automatically recognizable by the motion sensor 340 may include running, walking, swimming, cycling or rowing, which may be detectable through patterns in movement indicated by the movement sensor. According to various the embodiments, automatic recognition workout events may vary depending on the type of the wearable device 100, and the automatic recognition workout events may increase through connections between a plurality of devices. According to another embodiment, the processor 310 may determine the workout event based on a user's input which selects the workout event. For example, it may receive the user's input which selects the workout event through a user interface for selecting a workout list displayed through the display 120 and inputting the workout parameter (e.g., repetition times of a motion).

According to an embodiment, the processor 310 may determine the maximum heart rate (MHR) until the workout end event is detected after the workout start event occurs. For example, the processor 310 according to an embodiment may obtain heart rates in real time from the biometric waveform measured after the workout start event occurs and determine the maximum heart rate of the obtained heart rates. As another example, the processor 310 may determine the maximum heart rate by subtracting the user's age from 220. According to an embodiment, the processor 310 may determine intensity of a next workout based on a normal resting blood pressure (e.g., 60~80 bpm) and the determined maximum heart rate.

According to an embodiment, the processor 310 may detect occurrence of the workout end event based on a user's movement determined through the motion sensor 340. As another example, the processor 310 may determine that the workout is ended based on a user's input which ends the workout.

According to an embodiment, the processor 310 may calculate an average blood pressure value from blood pressure values after the workout end event occurrence. According to an embodiment, the processor 310 may determine a time point at which an error of the average blood pressure value of the post-workout period and the average blood pressure value of the normal period stays below a specific range for a specific time. For example, the average blood pressure value of the normal period may indicate an average blood pressure, if the normal resting blood pressure is maintained over a specific time in a daily life period excluding the sleeping period, the pre-workout period, the workout period, and the post-workout period.

According to an embodiment, the processor 310 may generate a workout parameter determination model. According to an embodiment of the present disclosure, in various embodiment of the present disclosure, the workout parameter determination model may indicate a prediction model configured to determine the workout parameter based on the obtained blood pressure value.

According to an embodiment, the processor 310 may generate the workout parameter generation model based on at least one of the profile information, the maximum heart rate, the conducted workout parameter and the continuous blood pressure value until the next workout. According to an embodiment, the processor 310 may determine the workout parameter based on the profile information provided from the profile analysis engine 413 before the learning by the machine learning engine 411 is performed. For example, the processor 310 may weight a plurality of values (e.g., the information provided from the blood pressure analysis engine 407, the heart rate analysis engine 409, the profile analysis engine 413 or the workout analysis engine 419) for determining the workout parameter. According to an embodiment, if reliability of the prediction model generated by the learning of the machine learning engine 411 is below a threshold (e.g., if the workout count is below a threshold), the processor 310 may increase the weight applied to the value provided from the profile analysis engine 413. According to an embodiment, the processor 310 may determine the workout parameter based on relations between the profile information, the maximum heart rate, the continuous blood pressure value and the conducted workout updated according to the learning of the machine learning engine 411 (e.g., an amount of the learning data is over a threshold). According to an embodiment, the processor 310 may analyze a user's blood pressure change according to the workout program configured with the determined workout parameter, and organize a next workout program based on the analysis result. According to an embodiment, the workout parameter may include a workout event, a workout count, a workout intensity, a workout time, a workout sequence and/or a ratio of an aerobic workout and an anaerobic workout. For example, the workout event may be determined through the automatic recognition function through the motion sensor 340, a manual input scheme according to a user input and/or a media content recognition function. Also, for example, the workout intensity may be determined based on the maximum heart rate, the workout event, the workout count, a workout duration time, a workout count per minute and/or the profile information.

The processor 310 according to an embodiment may display the information obtained based on the generated workout parameter determination model on the display 120, in operation 507.

According to an embodiment, the processor 310 may organize a workout program based on the determined workout parameter. According to an embodiment, the processor 310 may provide the organized workout program through an application. For example, the processor 310 may guide the workout event, count, time or sequence through the application. Also, for example, the processor 310 may guide the workout information in real time if determining that the user is working out. For example, the workout information may include at least one of a workout start time, a workout count, and a workout end time. Also, for example, the processor 310 may provide continuous blood pressure data or workout feedback. Detailed descriptions on a user interface (UI) provided through the display 120 shall be described later by referring to FIG. 10A through FIG. 10D.

According to an embodiment, the processor 310 may output a voice guidance or a sound through a speaker (e.g., a sound output module 1155 of FIG. 11). For example, if determining that the workout is finished, the processor 310 may guide a next workout according to the workout program using the sound. For example, the processor 310 may output the UI and the sound together.

According to an embodiment, the processor 310 may repeat operation 501 through operation 507.

Figure 5B:
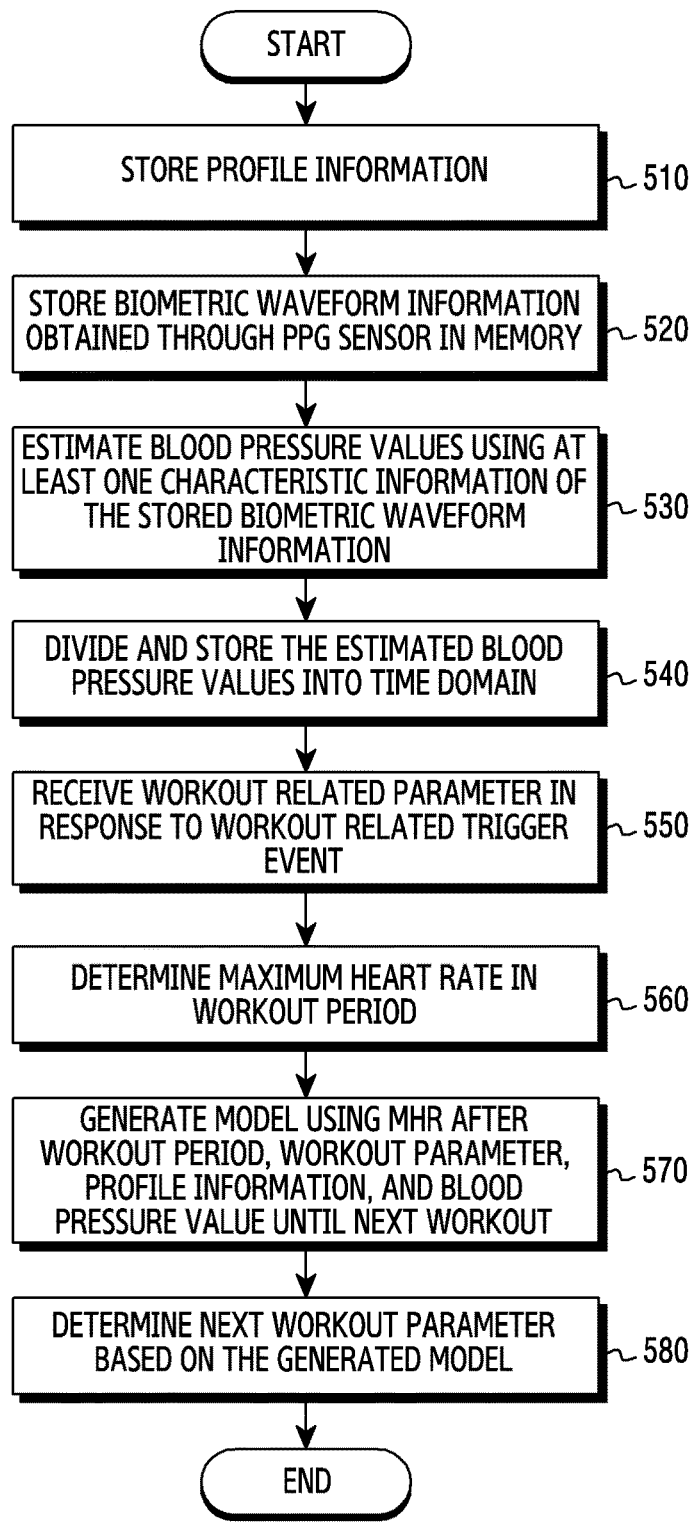
FIG. 5B is a flowchart of determining a workout parameter based on stored profile information and biometric data, in a wearable device according to an embodiment.

FIG. 5B is a flowchart of determining the workout parameter based on the stored profile information and biometric data, in the wearable device according to an embodiment. Details corresponding to or identical to and/or similar to the aforementioned details may be explained in brief or omitted with regard to descriptions of FIG. 5B.

Referring to FIG. 5B, the processor (e.g., the processor 310 of FIG. 3) according to an embodiment may store the user's profile information in operation 510.

According to an embodiment, the processor 310 may store the profile information such as the user's height, weight, age or gender and the blood pressure medicine medication information (e.g., information on whether or not to take medication, time to take medication, or type of medication) in the memory (e.g., the memory 330 of FIG. 3).

According to an embodiment, the processor 310 may store the biometric waveform information obtained through the PPG sensor 202 in the memory 330 in operation 520. According to an embodiment, the processor 310 may obtain PPG signal data through the strap (e.g., the strap 130 of FIG. 2) of the wearable device 100 which is worn on the user's body part (e.g., a wrist) and store it in the memory 330. According to an embodiment, the processor 310 may continuously obtain and store the PPG signal data in the memory 330.

According to an embodiment, the processor 310 may estimate the user's blood pressure values using at least one characteristic information of the stored biometric waveform information in operation 530. For example, the characteristic information of the biometric waveform information may include at least one of the maximum peak amplitude and the peak time index, the maximum peak amplitude and the peak time index of the systolic period, and the maximum peak amplitude and the peak time index of the diastolic period. According to an embodiment, the processor 310 may calculate the blood pressure value by calculating the difference or the ratio of the amplitude values of the stored biometric waveform and/or the difference between the time values.

According to an embodiment, the processor 310 may divide the blood pressure values according to a plurality of consecutive time periods (e.g., a time "domain") and store the estimated blood pressure values in operation 540. According to an embodiment, the processor 310 may continuously obtain the PPG signal, divide to PPG signal according to the plurality of consecutive time periods, and store them into a plurality of consecutive time periods. For example, the plurality of the consecutive time periods may include the normal period, the pre-workout period, the workout period, the post-workout period and the sleeping period, for which PPG signals received during each period may be stored in association with each period.

According to an embodiment, the processor 310 may obtain the blood pressure characteristic information of a designated measurement period (e.g., over 24 hours) from the blood pressure values estimated in operation 540. For example, the processor 310 may detect an event (e.g., a workout start event, a workout end event, a sleep start event, a sleep end event) for the measurement period using the motion sensor 340 and/or the biometric sensor 210. The processor 310 may divide the measurement period into a plurality of time periods according to the detected event, and obtain blood pressure information for each period. For example, the processor 310 may divide into four time periods (e.g., a normal period 810, a pre-workout period 820, a post-workout period 840 and a sleeping period 850 of FIG. 8), analyze (or detect) the blood pressure (e.g., at least one of a minimum blood pressure, a maximum blood pressure, and an average blood pressure) for each period and thus obtain the blood pressure characteristic information including at least part of the analysis result. For example, the blood pressure characteristic information may include information of at least part of the normal resting blood pressure, a blood pressure at 1 hour before the workout, the post-workout blood pressure (e.g., blood pressures per period with respect to consecutive periods after the workout, which are at least part of a period 1~2 hours after the workout, a period 2~3 hours after the workout, a period 3~4 hours after the workout, . . . , and a period 23~24 hours after the workout), or the blood pressure during the sleeping. According to an embodiment, the processor 310 may receive a current workout parameter in response to a workout related trigger event (e.g., a workout start event) in operation 550. The current workout parameter may be a parameter related to the user's workout conducted in the workout period (e.g., the workout period 830 of FIG. 8). According to an embodiment, the processor 310 may receive a current workout parameter in response to a workout related trigger event (e.g., a workout start event) in operation 550. The current workout parameter may be a parameter for the user's exercise performed during a workout period (e.g., the workout period 830 of FIG. 8). According to an embodiment, the processor 310 may detect a user's movement using the motion sensor 340. For example, the motion sensor 340 may include at least one of an accelerometer, a gyro sensor, a barometer or a magnetic sensor.

According to an embodiment, the processor 310 may receive a current workout parameter such as a workout event, a workout intensity, a workout count or a workout time in response to detecting the user's movement. For example, the processor 310 may determine the workout event to be at least one of running, walking, swimming, cycling, and/or rowing based on the user's movement.

According to an embodiment, the processor 310 may determine the maximum heart rate detected during the workout period in operation 560. According to an embodiment, the processor 310 may determine the maximum heart rate until detecting workout end event occurrence after the workout related trigger event (e.g., a workout start event) occurs. For example, the processor 310 according to an embodiment may determine the maximum heart rate by subtracting the stored user's age from 220.

According to an embodiment, after the workout period, the processor 310 may generate a model (e.g., a workout parameter determination model) using the maximum heart rate in the workout (or the maximum heart rate during the workout period), the current workout parameter (e.g., an event, an intensity, an aerobic/anaerobic workout ratio of the workout conducted in the workout period), user profile information (e.g., an age, a gender, a weight, a muscle mass, blood pressure medication information), and a blood pressure value until a next workout (or the post-workout period) in operation 570.

The model may be for mapping between the user's biometric information (e.g., the maximum heart rate during the workout, the blood pressure value after the workout, the user profile information) and the workout parameter (e.g., the workout event, the workout intensity). For example, the processor 310 may determine (or adjust) a next workout parameter based on the post-workout blood pressure value information stored in the model. The workout (or the current workout parameter) conducted in the workout period (e.g., the workout period 830 of FIG. 8) may affect a user's blood pressure change.

The model may store information (e.g., normal blood pressure holding time information, or weight information for workout parameter adjustment) indicating the effect of the conducted workout on the user's blood pressure change. The information may be calculated based on information of the post-workout blood pressure values. The information may be calculated further based on the maximum heart rate during the workout or the user profile information.

For example, the blood pressure immediately after the user has the aerobic workout may be lower than a normal resting blood pressure level, and the lowered blood pressure may last over a specific time and then return to the normal resting blood pressure level. For example, if the user is a hypertensive patient or a risk person, the normal resting blood pressure level of the user may be a higher level than the normal level, and the blood pressure falling after the workout may be the normal level.

The normal blood pressure holding time may correspond to a time for which the blood pressure falling after the workout is maintained below the normal resting blood pressure level. The normal blood pressure holding time may differ according to a user's condition (e.g., a cardiovascular state, an age, a gender, a weight, a muscle mass, blood pressure medication information).

The processor 310 may determine whether the normal blood pressure holding time exceeds a specific time (e.g., 2 hours). For example, the processor 310 may analyze blood pressure changes of the post-workout period and thus monitor whether an average blood pressure per period (or an average blood pressure per hour) falls below the normal resting blood pressure level over the specific time (e.g., 2 hours). The processor 310 may determine (or adjust) the next workout parameter based on the normal blood pressure holding time. For example, if the corresponding time is longer than a designated time, the current workout parameter (e.g., the workout event, the workout intensity) may be maintained or the next workout intensity may be maintained or lowered by applying a minus weight to the current workout parameter. As another example, if the corresponding time is shorter than a designated time, the next workout intensity may be increased by applying a plus weight to the current workout parameter. The next workout parameter may include at least part of a workout event, a workout count, a workout intensity, a workout time, a workout sequence and/or the ratio of the aerobic workout and the anaerobic workout of the workout to be conducted in a next workout period.

Figure 8:
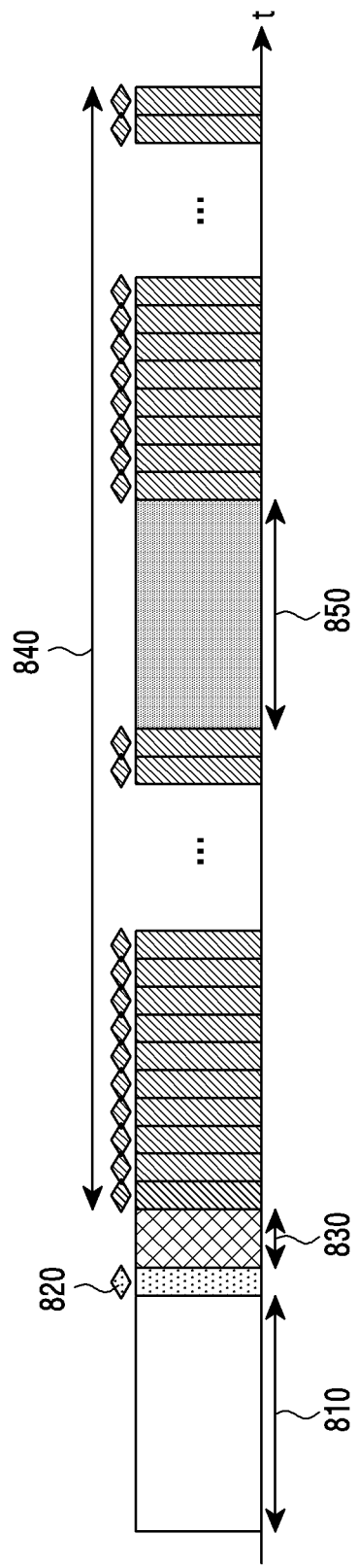
FIG. 8 is a diagram for illustrating storing a blood pressure value in a plurality of consecutive time periods in a wearable device of an embodiment.

In an embodiment, the processor 310 may determine the next workout parameter based on the blood pressure values (or blood pressure characteristic information) obtained for the post-workout period (e.g., at least part of the post-workout period 840 of FIG. 8). The processor 310 may provide adequate workout guide information to the user based on the determined workout parameter. The workout guide information may be for the user's blood pressure management (or control).

According to an embodiment, the processor 310 may generate a model using the detected maximum heart rate after the workout period, the workout parameter, the profile information, and the blood pressure value until the next workout in operation 570. According to an embodiment, the processor 310 may update the model based on a user profile change (e.g., a user's weight change) a blood pressure change according to the workout and the information learned at the machine learning engine 411.

According to an embodiment, the processor 310 may determine a workout parameter for a future workout session, based on the generated model in operation 580. According to an embodiment, the processor 310 may determine similarity or relationship between the workout events, and store the determined information and the difficulty of each workout in the workout data storage 405. According to an embodiment, the processor 310 may determine the workout parameter to be conducted based on the similarity, the relationship between the workout events and/or the difficulty of the workout. For example, the processor 310 may determine a workout (e.g., a push-up) having high similarity with an existing workout (e.g., a chin-up) and different difficulty as the workout to be conducted.

In an embodiment, the processor 310 may organize a workout program based on the next workout parameter. The processor 310 may provide the organized workout program through an application. For example, the processor 310 may display through the display 120 a UI (e.g., a fourth execution screen 1040 of FIG. 10D) for guiding the workout event, count, time or sequence of the workout to conduct next (e.g., a next workout period, next day, next week, next month) through the application.

Figure 6:
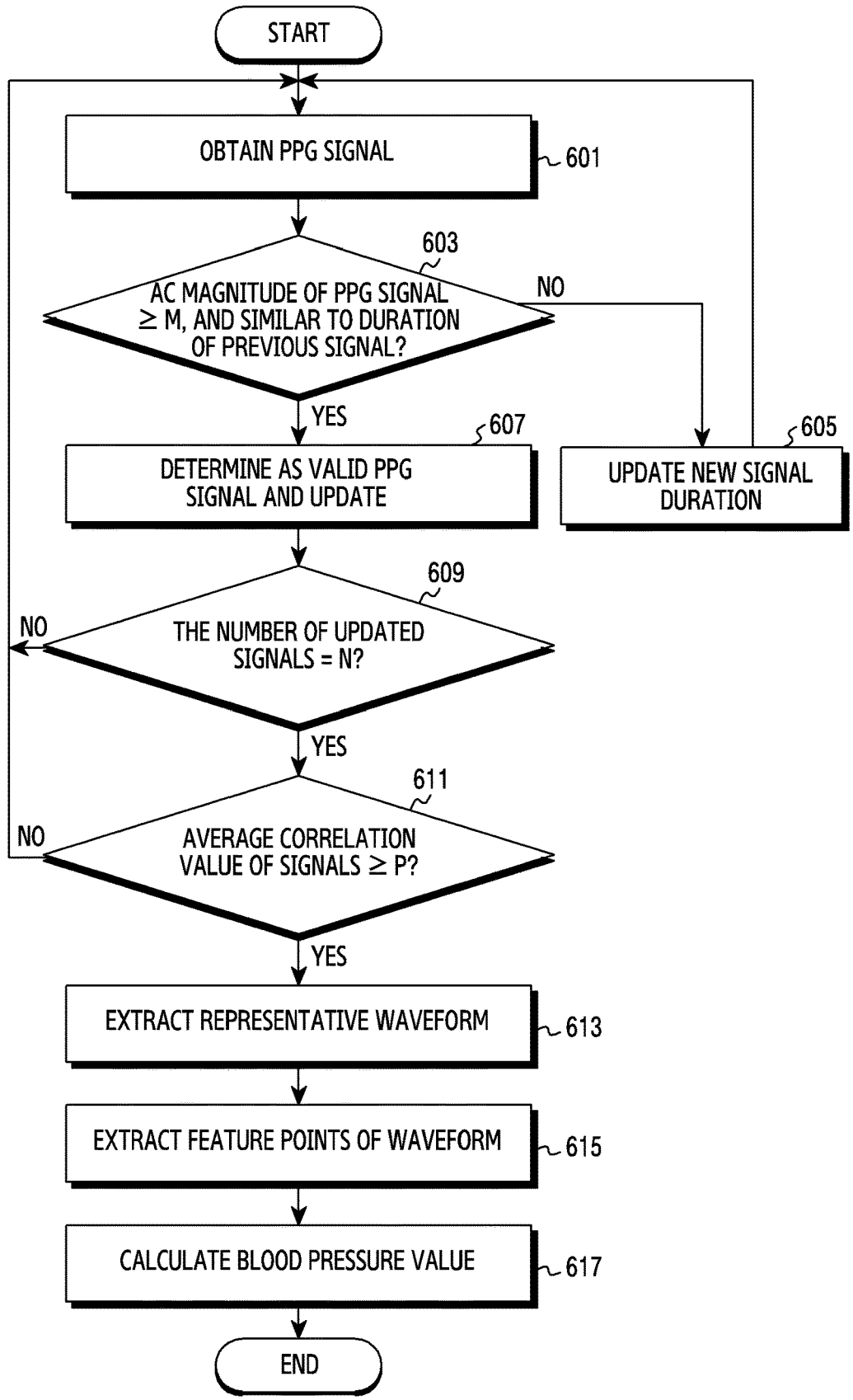
FIG. 6 is a flowchart of generating a blood pressure value based on obtained biometric data, in a wearable device according to an embodiment.

FIG. 6 is a flowchart of calculating a blood pressure value based on obtained biometric data, in a wearable device according to an embodiment. Details similar to or corresponding to the aforementioned details may be briefly explained or omitted in relation to the descriptions of FIG. 6.

Referring to FIG. 6, the processor (e.g., the processor 310 of FIG. 3) according to an embodiment may obtain a PPG signal data in operation 601. According to an embodiment, the wearable device 100 may obtain PPG signal data through the PPG sensor 202 as secured to a user's body using a strap (e.g., the strap 130 of FIG. 2) of the wearable device 100 and thus worn on the user's body part (e.g., a wrist). According to an embodiment, the PPG signal data may have a form of pulse beats. According to an embodiment, the processor 310 may continuously obtain the PPG signal data.

According to an embodiment, the processor 310 may compare an alternating current (AC) voltage magnitude of the PPG signal with a reference voltage magnitude M in operation 603. According to an embodiment, the reference voltage magnitude may be set to various values. According to an embodiment, the processor 310 may determine whether a duration of the obtained PPG signal is similar to a duration of a previously obtained PPG signal, in operation 603.

According to an embodiment, if determining that the AC voltage magnitude of the PPG signal is smaller than the reference voltage magnitude, or the duration of the obtained PPG signal is not similar to the duration of the previously obtained PPG signal, the processor 310 may determine the signal to be "valid," and update the new signal duration, in operation 605. For example, the processor 310 may update the new signal duration based on the duration of the obtained PPG signal. The processor 310 may update at new signal intervals and then return to operation 601, and obtain PPG signal data at the new signal intervals updated.

According to an embodiment, if determining that the AC voltage magnitude of the PPG signal is greater than or equal to the reference voltage magnitude, or the duration of the obtained PPG signal is similar to the duration of the previously obtained PPG signal, the processor 310 may update the obtained PPG signal, in operation 607.

According to an embodiment, the processor 310 may compare the number of the updated PPG signals with a reference number N in operation 609. For example, the reference number may be 15. Notably, the reference number is not limited thereto and it is understood that the reference number may be changed to various numbers.

According to an embodiment, if determining that the number of the updated PPG signals is not equal to the reference number, the processor 310 may return to operation 601 and obtain a PPG signal.

According to an embodiment, if determining that the number of the updated PPG signals is equal to the reference number in operation 609, the processor 310 may compare an average correlation value of the PPG signals with a reference correlation value P, in operation 611. For example, the reference correlation value may be 0.65, but again, the disclosure is not limited thereto.

According to an embodiment, if determining that the average correlation value of the obtained PPG signals is smaller than the reference correlation value, the processor 310 may return to operation 601 and obtain a new PPG signal.

According to an embodiment, if determining that the average correlation value of the PPG signals is greater than or equal to the reference correlation value in operation 611, the processor 310 may extract a representative waveform from the PPG signals, in operation 613. For example, the processor 310 may obtain an ensemble average of effective pulse beats, and acquire the representative waveform according to fluctuation of the obtained ensemble average.

According to an embodiment, the processor 310 may extract characteristic information of feature points of the representative waveform, in operation 615. For example, the characteristic information may include the maximum peak amplitude and the peak time index, the maximum peak amplitude and the peak time index of the systolic period, the maximum peak amplitude and the peak time index of the diastolic period and a total area.

According to an embodiment, the processor 310 may calculate the blood pressure value based on the extracted characteristic information in operation 617. For example, the processor 310 may calculate the blood pressure value using at least one of the characteristic information such as the maximum peak amplitude and the peak time index, the maximum peak amplitude and the peak time index of the systolic period, the maximum peak amplitude and the peak time index of the diastolic period and the total area.

According to an embodiment, the processor 310 may repeat execution of the operations shown in FIG. 6, and obtain the blood pressure value based on a waveform of dominant pulse beats in an array of the measured values. According to another embodiment, the processor 310 may execute the operations shown in FIG. 6 every designated time (e.g., 0 minutes every hour, or every 30 minutes).

Figure 7:
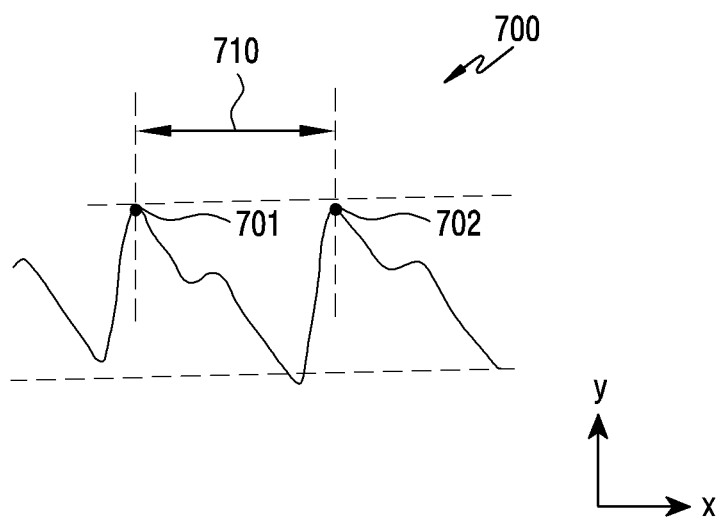
FIG. 7 is a diagram showing a photoplethysmogram (PPG) signal measured through a PPG sensor of a wearable device according to an embodiment.

FIG. 7 is a diagram showing a PPG signal measured through a PPG sensor 202 of a wearable device according to an embodiment.

Referring to FIG. 7, the X axis is a time axis, and the Y axis indicates a magnitude of a PPG signal 700 based on time with the voltage. According to an embodiment, as a blood flow rate in blood vessels in user's skins increases, a light absorption amount by the blood increases and the intensity of the PPG signal 700 measured through the PPG sensor 202 and received at a light receiving module (e.g., the light receiving module 204 of FIG. 2) (e.g., a PD) may reduce. If at least one LED of the PPG sensor 202 emits light, some light may reach user's arterial blood, venous blood, bones and/or skin tissues (e.g., epidermis and/or dermis). For example, part of the light reaching the arterial blood may be changed and absorbed due to a volume change of the arterial blood according to the user's pulse, and the wearable device 100 may detect part of that light upon reflection back towards the PPG sensor 202, and thereby obtain the PPG signal 700. The value of the PPG signal 700 may indicate a difference of a systolic blood flow rate and a diastolic blood flow rate of the user. The PPG signal 700 as shown may exhibit a maximum contraction point from a start point of left ventricle contraction, contraction decrease and aortic wall inflation point, a blood flow reduction point and an elastic wave of the valve and the myocardium. According to an embodiment, the processor 310 may extract a pulse cycle using the characteristic information such as maximum contraction points 701 and 702 of the left ventricle contraction from the PPG signal 700. For example, the pulse cycle may be measured by calculating a distance 710 between the maximum contraction points of the left ventricle contraction.

According to certain embodiments, the graph of the PPG signal 700 may be generated variously, and is not limited by the descriptions in certain embodiments of the present disclosure.

FIG. 8 is a diagram illustrating storing a blood pressure value in a plurality of consecutive time periods in a wearable device of an embodiment.

Referring to FIG. 8, the processor (e.g., the processor 310 of FIG. 3) according to an embodiment may divide the blood pressure values calculated based on the characteristic information of the PPG signal into a plurality of consecutive time periods and store them in the memory (e.g., the memory 330 of FIG. 3). For example, the plurality of the consecutive time periods may include a normal period 810, a pre-workout period 820, a workout period 830, a post-workout period 840 and a sleeping period 850. The pre-workout period 820 may in some embodiments indicate a period from 1 hour before the workout to the start of the workout, but is not limited thereto. For example, the post-workout period 840 may include a plurality of unit periods (e.g., 1-hour periods). The sleeping period 850 may be included in the post-workout period 840.

According to an embodiment, the processor 310 may exclude the blood pressure values of the workout period 830 from data used to estimate the workout conducted in the workout period 830. According to another embodiment, the processor 310 may not store the blood pressure values of the workout period 830 in the memory 330. According to an embodiment, the processor 310 may calculate in real time and store the blood pressure values of the post-workout period 840. According to another embodiment, the processor 310 may calculate and store the blood pressure values of the post-workout period 840 at specific time intervals (e.g., 5 minutes, 15 minutes, 30 minutes). According to an embodiment, the processor 310 may divide and store the blood pressure values of the post-workout period 840. For example, the processor 310 may divide and store the blood pressure values for 1-2 hours after the workout, the blood pressure values for 2-3 hours after the workout, or the blood pressure values for 3-4 hours after the workout. According to an embodiment, the processor 310 may calculate at least one of a minimum blood pressure value, a maximum blood pressure value and an average blood pressure value for each period.

Figure 9:
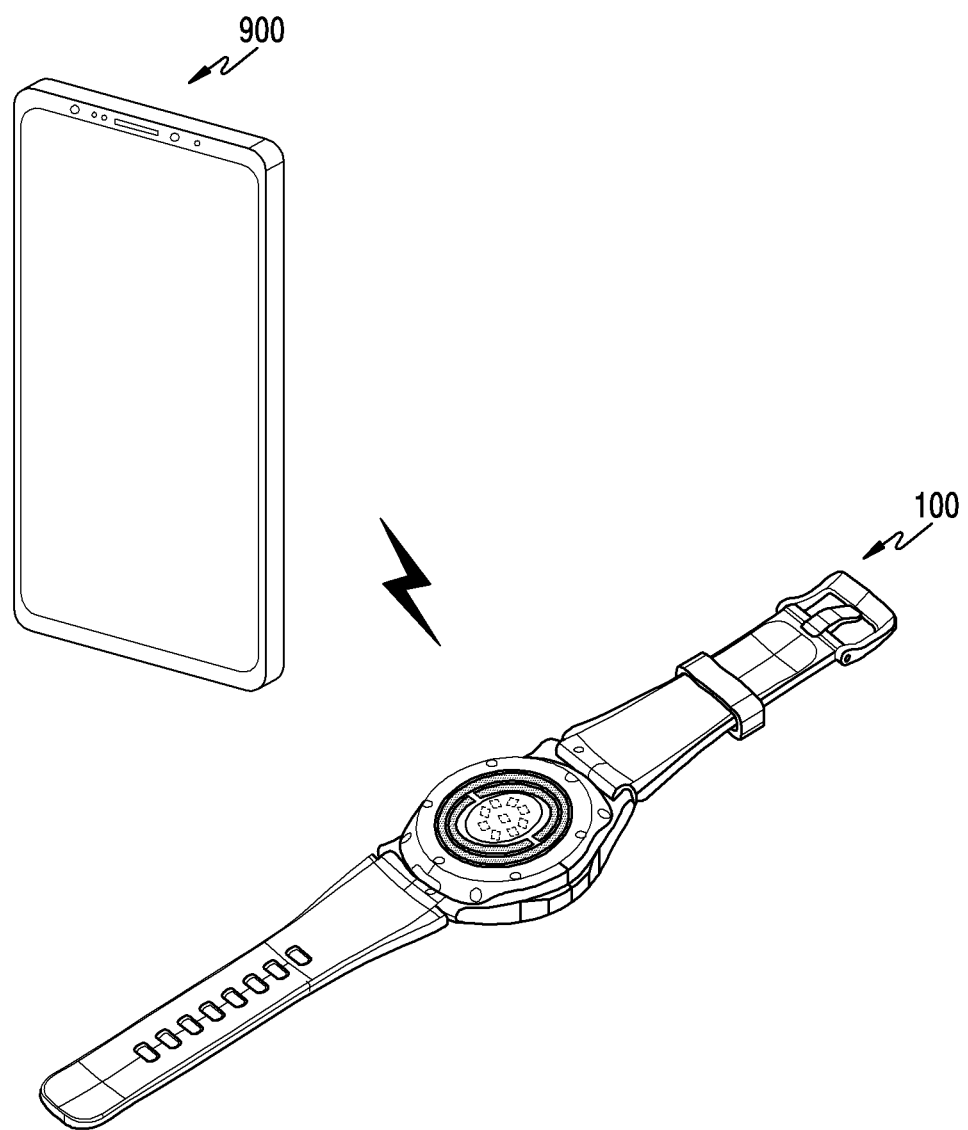
FIG. 9 illustrates an environment where a wearable device and an electronic device operate according to an embodiment.

FIG. 9 illustrates an environment where a wearable device and an electronic device operate according to an embodiment.

Referring to FIG. 9, the wearable device 100 and an electronic device 900 according to an embodiment may interoperate. For example, the wearable device 100 may include at least one of a smart watch, earbuds, a ring, glasses, or shoes, and the electronic device 900 may indicate a smart phone. According to an embodiment, the wearable device 100 and the electronic device 900 may provide the user with a service which aids in execution of the workout program, including various workout parameters (e.g., a workout event, a workout intensity, a workout difficulty).

According to an embodiment, the wearable device 100 may transmit to the electronic device 900 the PPG signal data obtained through the PPG sensor 202 and/or the workout information obtained through the motion sensor 340. According to an embodiment, the PPG signal data and/or the workout information stored in the wearable device 100 and/or the PPG signal data and/or the workout information stored in the electronic device 900 may be synchronized. According to an embodiment, if a target quantity of a workout motion (e.g., a particular exercise) included in the workout program is achieved (e.g., the exercise is performed for the set number of repetitions), the wearable device 100 may control the electronic device 900 to output content corresponding to a next workout motion (e.g., a next exercise) included in the workout program.

The electronic device 900 according to an embodiment may be wirelessly connected with the wearable device 100. The wearable device 100 may be connected with the electronic device 900 via a short-range network supportable by a communication circuit (e.g., the communication circuit 320 of FIG. 3), and transmit and/or receive data. For example, the network (e.g., a short-range network) for establishing the connection between the wearable device 100 and the electronic device 900 may be adequately selected. For example, together with Bluetooth or in lieu of Bluetooth, Bluetooth low energy (BLE), Wi-Fi direct, NFC, ultra-wide band (UWB) communication, or infra-red communication may be used to establish the connection between the wearable device 100 and the electronic device 900. According to an embodiment, the electronic device 900 may obtain information of the workout program to conduct from the wearable device 100. The workout program information in the electronic device 900 may be the same information as the workout program information in the wearable device 100.

According to an embodiment, the electronic device 900 may output content corresponding to one workout motion (e.g., a single exercise) of a plurality of workout motions included in the workout program. For example, the electronic device 900 may output contents corresponding to a squat motion.

According to an embodiment, the electronic device 900 may output content corresponding to a next workout motion (e.g., a next exercise in a preset sequence of exercises) under the control of the wearable device 100. For example, if receiving a control message from the wearable device 100 while outputting the contents corresponding to the squat motion, the electronic device 900 may output content corresponding to a walking motion which is the next workout motion.

Figure 10A:
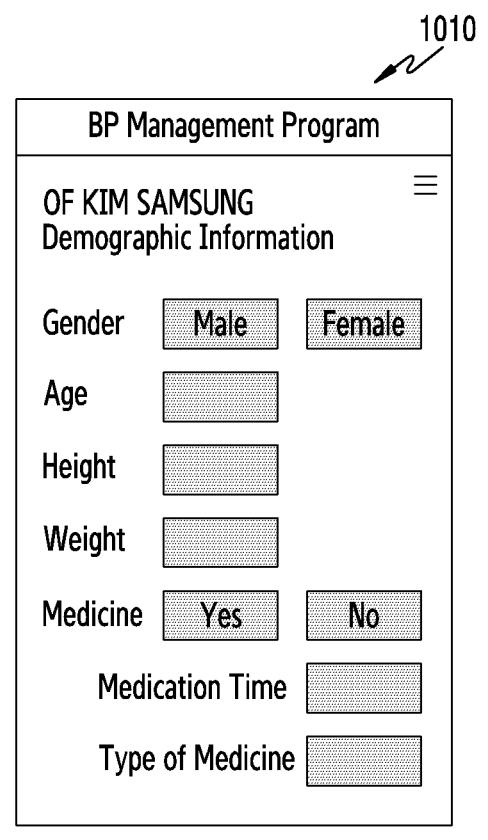

FIG. 10A is a diagram for showing a UI displayed on a display, in an electronic device according to a first embodiment.

Referring to FIG. 10A, the electronic device 900 according to an embodiment may output a first execution screen 1010 through an application. According to an embodiment, the electronic device 900 may output content related to the user's profile information such as the user's gender, age, height, weight, or blood pressure medicine information (e.g., medication time, medication type) in the first execution screen 1010. For example, the electronic device 900 may output the first execution screen 1010 to the display, for facilitating input of the user's profile information in to the electronic device 900. As another example, the electronic device 900 may output the first execution screen 1010 on the display with the user's profile information already filled-in, to indicating the inputted profile information.

Figure 10B:
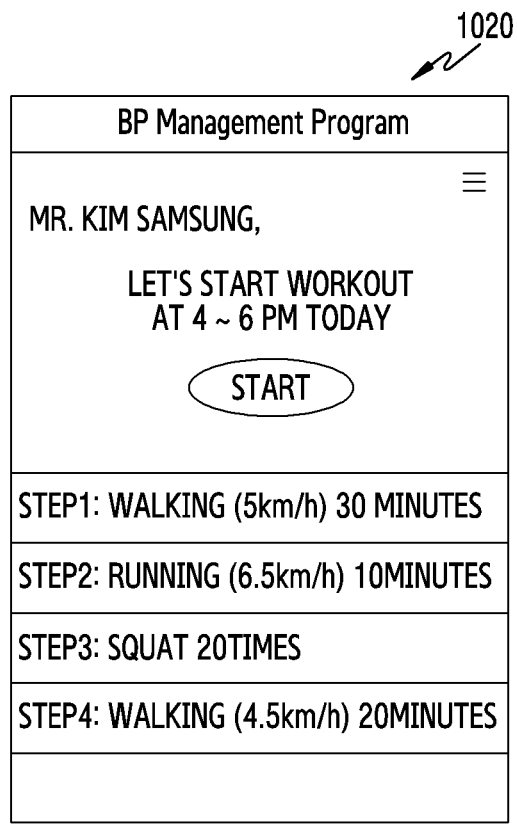
FIG. 10B is a diagram for showing a UI displayed on a display, in an electronic device according to a second embodiment.

FIG. 10B is a diagram for showing a UI displayed on the display, in the electronic device according to a second embodiment.

Referring to FIG. 10B, the wearable device 100 according to an embodiment may control the electronic device 900 to output a second execution screen 1020, which may include content corresponding to a workout program. According to an embodiment, the workout program provided through the second execution screen 1020 may be configured based on the PPG signal data obtained by the PPG sensor 202 and the workout information obtained through the motion sensor 340. For example, the workout program may include a workout parameter such as a workout event, a workout sequence, a workout time or workout difficulty. According to an embodiment, if a target amount of a workout motion included in the workout program is achieved, the wearable device 100 may control the electronic device 900 to output content corresponding to a next workout motion (e.g., moving on to a next exercise in a preset sequence of exercises forming the workout). According to an embodiment, the electronic device 900 may output a voice guidance or a sound through the speaker. For example, if determining that a particular exercise is finished, the electronic device 900 may provide guidance for a next exercise according to the workout program using the sound. According to an embodiment, the electronic device 900 may output the UI and the sound together.

Figure 10C:
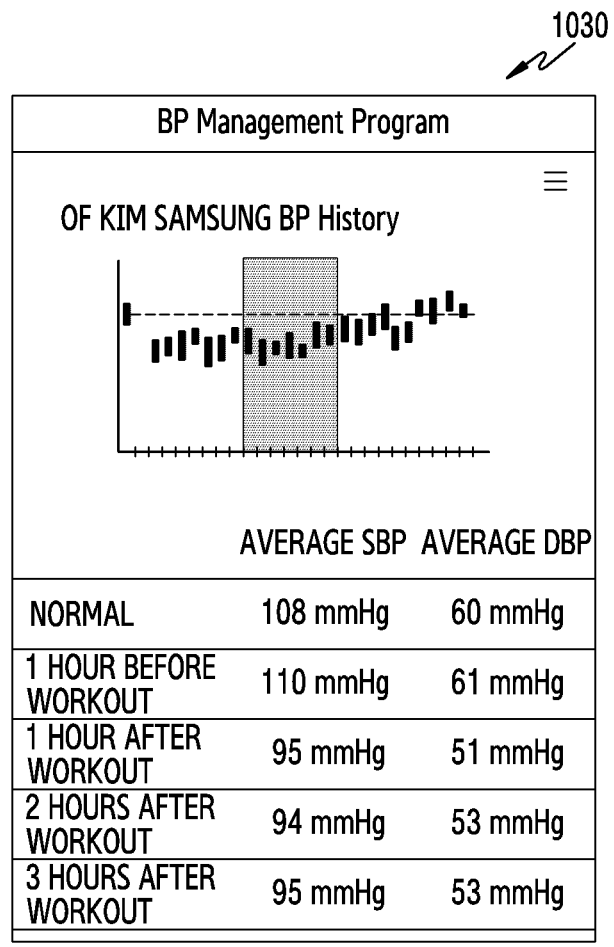
FIG. 10C is a diagram for showing a UI displayed on a display, in an electronic device according to a third embodiment.

FIG. 10C is a diagram for showing a UI displayed on the display, in the electronic device according to a third embodiment.

Referring to FIG. 10C, the wearable device 100 according to an embodiment may control the electronic device 900 to output a third execution screen 1030, including the blood pressure value obtained by the wearable device 100. According to an embodiment, the electronic device 900 may display a visualization of continuous monitoring of blood pressure value over time. According to an embodiment, the electronic device 900 may provide the blood pressure value calculated in a plurality of consecutive time periods. For example, the electronic device 900 may output the third execution screen 1030 including average blood pressure values of a normal period, a 1-hour period before workout, a 1-hour period after workout, a 2-hour period after workout, and a 3-hour period after workout. For example, the electronic device 900 may provide an average systolic blood pressure (SBP) and an average diastolic blood pressure (DBP) for each period.

Figure 10D:
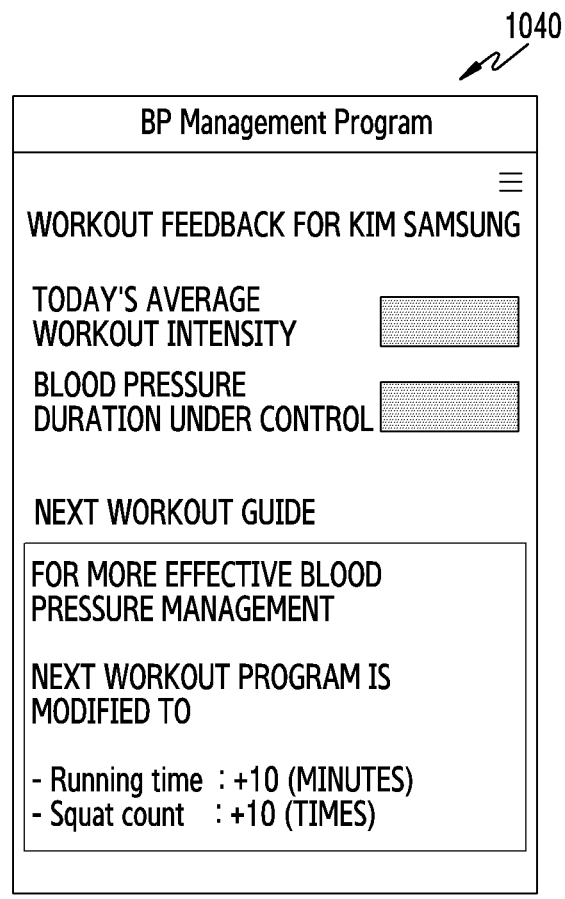
FIG. 10D is a diagram for showing a UI displayed on a display, in an electronic device according to a fourth embodiment.

FIG. 10D is a diagram for showing a UI displayed on the display, in the electronic device according to a fourth embodiment.

Referring to FIG. 10D, the wearable device 100 according to an embodiment may control the electronic device 900 to output a fourth execution screen 1040, including content corresponding to workout feedback. For example, the fourth execution screen 1040 may include workout parameters related to the conducted workout. Also, for example, the fourth execution screen 1040 may include contents corresponding to a next workout program as generated based on the blood pressure values measured in the post-workout period. As seen therein, the next workout program may include adjustments to the previous workout, such as an increase in repetitions or time, in the event the workout was detected as insufficiently challenging for the user.

According to an embodiment, the execution screens 1010, 1020, 1030 and 1040 shown in FIG. 10A through FIG. 10D may be outputted through the display 120 of the wearable device 100. According to an embodiment, the execution screens 1010, 1020, 1030 and 1040 may be outputted by changing their resolution and size according to the size of the display 120 of the wearable device 100.

According to the above embodiment, the wearable device 100 may support the user to frequently identify his/her health condition in daily life, and provide various workout programs to improve the health condition. The health condition improvement may indicate improvement of the physiological state (e.g., a cardiovascular state) and/or the physical state (e.g., the muscle mass, the weight, etc.) of the user.

In addition, according to the above embodiment, the wearable device 100 may support the user to continuously monitor the blood pressure change according to the workout, provide an adequate workout program to the user by suggesting the feedback based on the relation between the workout and the blood pressure change, and thus support improving the user's health condition.

FIG. 11 is a block diagram illustrating an electronic device 1101 in a network environment 1100 according to certain embodiments. Referring to FIG. 11, the electronic device 1101 in the network environment 1100 may communicate with an electronic device 1102 via a first network 1198 (e.g., a short-range wireless communication network), or at least one of an electronic device 1104 or a server 1108 via a second network 1199 (e.g., a long-range wireless communication network). According to an embodiment, the electronic device 1101 may communicate with the electronic device 1104 via the server 1108. According to an embodiment, the electronic device 1101 may include a processor 1120, memory 1130, an input module 1150, a sound output module 1155, a display module 1160, an audio module 1170, a sensor module 1176, an interface 1177, a connecting terminal 1178, a haptic module 1179, a camera module 1180, a power management module 1188, a battery 1189, a communication module 1190, a subscriber identification module (SIM) 1196, or an antenna module 1197. In some embodiments, at least one of the components (e.g., the connecting terminal 1178) may be omitted from the electronic device 1101, or one or more other components may be added in the electronic device 1101. In some embodiments, some of the components (e.g., the sensor module 1176, the camera module 1180, or the antenna module 1197) may be implemented as a single component (e.g., the display module 1160).

The processor 1120 may execute, for example, software (e.g., a program 1140) to control at least one other component (e.g., a hardware or software component) of the electronic device 1101 coupled with the processor 1120, and may perform various data processing or computation. According to an embodiment, as at least part of the data processing or computation, the processor 1120 may store a command or data received from another component (e.g., the sensor module 1176 or the communication module 1190) in volatile memory 1132, process the command or the data stored in the volatile memory 1132, and store resulting data in non-volatile memory 1134. According to an embodiment, the processor 1120 may include a main processor 1121 (e.g., a central processing unit (CPU) or an application processor (AP)), or an auxiliary processor 1123 (e.g., a graphics processing unit (GPU), a neural processing unit (NPU), an image signal processor (ISP), a sensor hub processor, or a communication processor (CP)) that is operable independently from, or in conjunction with, the main processor 1121. For example, when the electronic device 1101 includes the main processor 1121 and the auxiliary processor 1123, the auxiliary processor 1123 may be adapted to consume less power than the main processor 1121, or to be specific to a specified function. The auxiliary processor 1123 may be implemented as separate from, or as part of the main processor 1121.

The auxiliary processor 1123 may control at least some of functions or states related to at least one component (e.g., the display module 1160, the sensor module 1176, or the communication module 1190) among the components of the electronic device 1101, instead of the main processor 1121 while the main processor 1121 is in an inactive (e.g., sleep) state, or together with the main processor 1121 while the main processor 1121 is in an active state (e.g., executing an application). According to an embodiment, the auxiliary processor 1123 (e.g., an image signal processor or a communication processor) may be implemented as part of another component (e.g., the camera module 1180 or the communication module 1190) functionally related to the auxiliary processor 1123. According to an embodiment, the auxiliary processor 1123 (e.g., the neural processing unit) may include a hardware structure specified for artificial intelligence model processing. An artificial intelligence model may be generated by machine learning. Such learning may be performed, e.g., by the electronic device 1101 where the artificial intelligence is performed or via a separate server (e.g., the server 1108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 1130 may store various data used by at least one component (e.g., the processor 1120 or the sensor module 1176) of the electronic device 1101. The various data may include, for example, software (e.g., the program 1140) and input data or output data for a command related thererto. The memory 1130 may include the volatile memory 1132 or the non-volatile memory 1134.

The program 1140 may be stored in the memory 1130 as software, and may include, for example, an operating system (OS) 1142, middleware 1144, or an application 1146.

The input module 1150 may receive a command or data to be used by another component (e.g., the processor 1120) of the electronic device 1101, from the outside (e.g., a user) of the electronic device 1101. The input module 1150 may include, for example, a microphone, a mouse, a keyboard, a key (e.g., a button), or a digital pen (e.g., a stylus pen).

The sound output module 1155 may output sound signals to the outside of the electronic device 1101. The sound output module 1155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 1160 may visually provide information to the outside (e.g., a user) of the electronic device 1101. The display module 1160 may include, for example, a display, a hologram device, or a projector and control circuitry to control a corresponding one of the display, hologram device, and projector. According to an embodiment, the display module 1160 may include a touch sensor adapted to detect a touch, or a pressure sensor adapted to measure the intensity of force incurred by the touch.

The audio module 1170 may convert a sound into an electrical signal and vice versa. According to an embodiment, the audio module 1170 may obtain the sound via the input module 1150, or output the sound via the sound output module 1155 or a headphone of an external electronic device (e.g., an electronic device 1102) directly (e.g., wiredly) or wirelessly coupled with the electronic device 1101.

The sensor module 1176 may detect an operational state (e.g., power or temperature) of the electronic device 1101 or an environmental state (e.g., a state of a user) external to the electronic device 1101, and then generate an electrical signal or data value corresponding to the detected state. According to an embodiment, the sensor module 1176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1177 may support one or more specified protocols to be used for the electronic device 1101 to be coupled with the external electronic device (e.g., the electronic device 1102) directly (e.g., wiredly) or wirelessly. According to an embodiment, the interface 1177 may include, for example, a high definition multimedia interface (HDMI), a universal serial bus (USB) interface, a secure digital (SD) card interface, or an audio interface.

A connecting terminal 1178 may include a connector via which the electronic device 1101 may be physically connected with the external electronic device (e.g., the electronic device 1102). According to an embodiment, the connecting terminal 1178 may include, for example, a HDMI connector, a USB connector, a SD card connector, or an audio connector (e.g., a headphone connector).

The haptic module 1179 may convert an electrical signal into a mechanical stimulus (e.g., a vibration or a movement) or electrical stimulus which may be recognized by a user via his tactile sensation or kinesthetic sensation. According to an embodiment, the haptic module 1179 may include, for example, a motor, a piezoelectric element, or an electric stimulator.

The camera module 1180 may capture a still image or moving images. According to an embodiment, the camera module 1180 may include one or more lenses, image sensors, image signal processors, or flashes.

The power management module 1188 may manage power supplied to the electronic device 1101. According to an embodiment, the power management module 1188 may be implemented as at least part of, for example, a power management integrated circuit (PMIC).

The battery 1189 may supply power to at least one component of the electronic device 1101. According to an embodiment, the battery 1189 may include, for example, a primary cell which is not rechargeable, a secondary cell which is rechargeable, or a fuel cell.

The communication module 1190 may support establishing a direct (e.g., wired) communication channel or a wireless communication channel between the electronic device 1101 and the external electronic device (e.g., the electronic device 1102, the electronic device 1104, or the server 1108) and performing communication via the established communication channel. The communication module 1190 may include one or more communication processors that are operable independently from the processor 1120 (e.g., the application processor (AP)) and supports a direct (e.g., wired) communication or a wireless communication. According to an embodiment, the communication module 1190 may include a wireless communication module 1192 (e.g., a cellular communication module, a short-range wireless communication module, or a global navigation satellite system (GNSS) communication module) or a wired communication module 1194 (e.g., a local area network (LAN) communication module or a power line communication (PLC) module). A corresponding one of these communication modules may communicate with the external electronic device via the first network 1198 (e.g., a short-range communication network, such as Bluetooth™, wireless-fidelity (Wi-Fi) direct, or infrared data association (IrDA)) or the second network 1199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1192 may identify and authenticate the electronic device 1101 in a communication network, such as the first network 1198 or the second network 1199, using subscriber information (e.g., international mobile subscriber identity (IMSI)) stored in the subscriber identification module 1196.

The wireless communication module 1192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 1192 may support a high-frequency band (e.g., the mmWave band) to achieve, e.g., a high data transmission rate. The wireless communication module 1192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 1192 may support various requirements specified in the electronic device 1101, an external electronic device (e.g., the electronic device 1104), or a network system (e.g., the second network 1199). According to an embodiment, the wireless communication module 1192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 1197 may transmit or receive a signal or power to or from the outside (e.g., the external electronic device) of the electronic device 1101. According to an embodiment, the antenna module 1197 may include an antenna including a radiating element implemented using a conductive material or a conductive pattern formed in or on a substrate (e.g., a printed circuit board (PCB)). According to an embodiment, the antenna module 1197 may include a plurality of antennas (e.g., array antennas). In such a case, at least one antenna appropriate for a communication scheme used in the communication network, such as the first network 1198 or the second network 1199, may be selected, for example, by the communication module 1190 (e.g., the wireless communication module 1192) from the plurality of antennas. The signal or the power may then be transmitted or received between the communication module 1190 and the external electronic device via the selected at least one antenna. According to an embodiment, another component (e.g., a radio frequency integrated circuit (RFIC)) other than the radiating element may be additionally formed as part of the antenna module 1197.

According to certain embodiments, the antenna module 1197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 1101 and the external electronic device 1104 via the server 1108 coupled with the second network 1199. Each of the electronic devices 1102 or 1104 may be a device of a same type as, or a different type, from the electronic device 1101. According to an embodiment, all or some of operations to be executed at the electronic device 1101 may be executed at one or more of the external electronic devices 1102, 1104, or 1108. For example, if the electronic device 1101 should perform a function or a service automatically, or in response to a request from a user or another device, the electronic device 1101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1101. The electronic device 1101 may provide the outcome, with or without further processing of the outcome, as at least part of a reply to the request. To that end, a cloud computing, distributed computing, mobile edge computing (MEC), or client-server computing technology may be used, for example. The electronic device 1101 may provide ultra-low-latency services using, e.g., distributed computing or mobile edge computing. In another embodiment, the external electronic device 1104 may include an internet-of-things (IoT) device. The server 1108 may be an intelligent server using machine learning and/or a neural network. According to an embodiment, the external electronic device 1104 or the server 1108 may be included in the second network 1199. The electronic device 1101 may be applied to intelligent services (e.g., smart home, smart city, smart car, or healthcare) based on 5G communication technology or IoT-related technology.

The electronic device according to certain embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that certain embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used in connection with certain embodiments of the disclosure, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Certain embodiments as set forth herein may be implemented as software (e.g., the program 1140) including one or more instructions that are stored in a storage medium (e.g., internal memory 1136 or external memory 1138) that is readable by a machine (e.g., the electronic device 1101). For example, a processor (e.g., the processor 1120) of the machine (e.g., the electronic device 1101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to certain embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to certain embodiments, each component (e.g., a module or a program) of the above-described components may include a single entity or multiple entities, and some of the multiple entities may be separately disposed in different components. According to certain embodiments, one or more of the above-described components may be omitted, or one or more other components may be added. Alternatively or additionally, a plurality of components (e.g., modules or programs) may be integrated into a single component. In such a case, according to certain embodiments, the integrated component may still perform one or more functions of each of the plurality of components in the same or similar manner as they are performed by a corresponding one of the plurality of components before the integration. According to certain embodiments, operations performed by the module, the program, or another component may be carried out sequentially, in parallel, repeatedly, or heuristically, or one or more of the operations may be executed in a different order or omitted, or one or more other operations may be added.

As stated above, a wearable device (e.g., the wearable device 100 of FIG. 1) according to an embodiment may include a memory (e.g., the memory 330 of FIG. 3), a housing (e.g., the housing 110 of FIG. 2), a PPG sensor (e.g., the PPG sensor 202 of FIG. 2) exposed through at least part of the housing, a display (e.g., the display 120 of FIG. 2) and at least one processor (e.g., the processor 310 of FIG. 3) operatively connected with the display, the memory and the PPG sensor, and the at least one processor may obtain a PPG signal through the PPG sensor, obtain blood pressure values of a plurality of consecutive time periods based on characteristic information of the obtained PPG signal, after a workout start event occurs, in response to occurrence of a workout end event, generate a workout parameter determination model based on blood pressure characteristic information obtained from the blood pressure values after the workout end event occurrence, and display information obtained based on the generated workout parameter determination model through the display.

In the wearable device 100 according to an embodiment, the characteristic information of the PPG signal may include at least one of a duration, an amplitude, and morphology of the obtained PPG signal.

The wearable device 100 according to an embodiment may include a motion sensor, and obtain workout details information through the motion sensor.

According to an embodiment, the motion sensor may include at least one of an accelerometer, a gyro sensor, a barometer, or a magnetic sensor.

According to an embodiment, the workout details information may include at least one of a workout type, a workout count, and a maximum heart rate value.

The wearable device 100 according to an embodiment may, in response to the occurrence of the workout start event, generate the workout parameter determination model based on a relation between the workout details information obtained through the motion sensor and the blood pressure characteristic information.

The wearable device 100 according to an embodiment may update the workout parameter determination model through machine learning on the relation between the workout details information and the blood pressure characteristic information.

The wearable device 100 according to an embodiment may store medication time information in the memory, and determine a relation between the blood pressure characteristic information and the workout details information based on the stored medication time information.

According to an embodiment, the at least one processor may automatically obtain the PPG signal, in response to determining that a user wears the wearable device.

According to an embodiment, the at least one processor may obtain the PPG signal in response to detecting a measurement mode.

According to an embodiment, the at least one processor may obtain the blood pressure values using a pulse wave analysis (PWA) scheme which determines the blood pressure value based on an analysis result of a waveform of the PPG signal.

The wearable device 100 according to an embodiment may further include an ECG sensor, and the at least one processor may obtain an ECG signal through the ECG sensor, and obtain the blood pressure values using a pulse wave velocity (PWV) scheme which determines the blood pressure value by comparing the obtained PPG signal and the obtained ECG signal.

An operation method of a wearable device (e.g., the wearable device 100 of FIG. 1) according to an embodiment as stated above may include obtaining a PPG signal through a PPG sensor (e.g., the PPG sensor 202 of FIG. 2), obtaining blood pressure values of a plurality of consecutive time periods based on characteristic information of the obtained PPG signal, after a workout start event occurs, in response to occurrence of a workout end event, generating a workout parameter determination model based on blood pressure characteristic information obtained from the blood pressure values after the workout end event occurrence, and displaying information obtained based on the generated workout parameter determination model through a display.

The operation method of the wearable device according to an embodiment may include obtaining workout details information through a motion sensor.

The operation method of the wearable device according to an embodiment may obtaining workout details information through a motion sensor.

As stated above, an electronic device (e.g., the electronic device 900 of FIG. 9) according to an embodiment may include a memory, a communication circuit configured to communicate with a wearable device, a display, and at least one processor operatively connected with the display, the communication circuit and the display, and the at least one processor may receive a PPG signal value from the wearable device, through the communication circuit, obtain blood pressure values of a plurality of consecutive time periods based on the PPG signal value, after a workout start event occurs, in response to occurrence of a workout end event, generate a workout parameter determination model based on blood pressure characteristic information of blood pressure values after the workout end event occurrence, and display information obtained based on the generated workout parameter determination model through the display.

The electronic device 900 according to an embodiment may receive workout details information from the wearable device, through the communication circuit.

The electronic device 900 according to an embodiment may, in response to the occurrence of the workout start event, generate the workout parameter determination model based on a relation between the workout details information and the blood pressure characteristic information.

The electronic device 900 according to an embodiment may update the workout parameter determination model through machine learning on the relation between the workout details information and the blood pressure characteristic information.

The electronic device 900 according to an embodiment may store medication time information in the memory, and determine a relation between the workout details information and the blood pressure characteristic information based on the stored medication time information.

What is claimed is:

1. A wearable device, comprising:
   a memory;
   a housing;
   a photoplethysmogram (PPG) sensor exposed to an external environment of the wearable device through at least part of the housing;
   a display; and
   at least one processor operatively connected with the display, the memory and the PPG sensor, wherein the at least one processor is configured to:
   receive a PPG signal via the PPG sensor,
   detect blood pressure values for a plurality of consecutive time periods based on characteristic information detected from the received PPG signal,
   in response to detecting termination of an exercise event, generate an exercise parameter determination model based on blood pressure characteristic information generated from the detected blood pressure values after the detected termination, and
   control the display to display information generated from the exercise parameter determination model.

2. The wearable device of claim 1, wherein the characteristic information detected from the received PPG signal includes at least one of a duration, an amplitude, and morphology of the received PPG signal.

3. The wearable device of claim 1, further comprising:
   a motion sensor,
   wherein detailed information on the exercise event is derived from movements detected through the motion sensor.

4. The wearable device of claim 3, wherein the motion sensor includes at least one of an accelerometer, a gyro sensor, a barometer, or a magnetic sensor.

5. The wearable device of claim 3, wherein the detailed information on the exercise event includes at least one of an exercise type, a count of movements performed, and a maximum heart rate value.

6. The wearable device of claim 3, wherein the exercise parameter determination model is generated based on a relationship between the detailed information on the exercise event detected through the motion sensor, and the blood pressure characteristic information.

7. The wearable device of claim 6, wherein the at least one processor is further configured to:
   update the exercise parameter determination model via machine learning, based on the relationship between the detailed information on the exercise event, and the blood pressure characteristic information.

8. The wearable device of claim 3, wherein the at least one processor is further configured to:
   store medication time information in the memory,
   determine a relationship between the blood pressure characteristic information and the detailed information on the exercise event, based at least partially on the stored medication time information.

9. The wearable device of claim 1, wherein the PPG signal is automatically received, in response to detecting that a user is wearing the wearable device.

10. The wearable device of claim 1, wherein the PPG signal is received in response to detecting execution of a measurement mode of the wearable device.

11. The wearable device of claim 1, wherein the blood pressure values are detected using a pulse wave analysis (PWA) scheme, including analyzing a waveform of the PPG signal.

12. The wearable device of claim 1, further comprising:
   an electrocardiography (ECG) sensor,
   wherein the at least one processor is further configured to:
   receive an ECG signal via the ECG sensor,
   wherein the blood pressure values are detected using a pulse wave velocity (PWV) scheme which includes comparing the received PPG signal to the received ECG signal.

13. An method of a wearable device, comprising:
   receiving a photoplethysmogram (PPG) signal via a PPG sensor;
   receiving blood pressure values for a plurality of consecutive time periods based on characteristic information detected from the received PPG signal;
   in response to detecting termination of an exercise event, generating an exercise parameter determination model based on blood pressure characteristic information generated from the received blood pressure values after the detected termination; and
   displaying information generated from the exercise parameter determination model on a display.

14. The wearable device of claim 13, further comprising:
   detecting movements related to the exercise event via a motion sensor,
   wherein detailed information on the exercise event is derived from the detected movements.

15. The wearable device of claim 14, wherein the motion sensor includes at least one of an accelerometer, a gyro sensor, a barometer, or a magnetic sensor.

16. An electronic device, comprising:
   a memory;
   a communication circuit configured to communicate with a wearable device;
   a display; and
   at least one processor operatively connected with the display, the communication circuit and the display,
   wherein the at least one processor is configured to:
   receive a photoplethysmogram (PPG) signal value from the wearable device, via the communication circuit,
   detect blood pressure values for a plurality of consecutive time periods based on the PPG signal value,
   in response to detecting termination of an exercise event, generate an exercise parameter determination model based on blood pressure characteristic information generated from the detected blood pressure values after the detected termination, and
   display information generated from the exercise parameter determination model.

17. The electronic device of claim 16, wherein the at least one processor is further configured to:
   receive detailed information on the exercise event as detected by the wearable device, via the communication circuit.

18. The electronic device of claim 17, wherein the exercise parameter determination model is generated based on a relationship between the detailed information on the exercise event and the blood pressure characteristic information.

19. The electronic device of claim 18, wherein the at least one processor is further configured to:
   update the exercise parameter determination model via machine learning based on the relationship between the detailed information of the exercise event, and the blood pressure characteristic information.

20. The electronic device of claim 17, wherein the at least one processor is further configured to:
   store medication time information in the memory, and
   determine a relationship between the detailed information on the exercise event and the blood pressure characteristic information, based on the stored medication time information.

* * * * *